(12) United States Patent
Molaei

(10) Patent No.: US 12,089,863 B2
(45) Date of Patent: *Sep. 17, 2024

(54) MULTI-PIVOT THROMBECTOMY DEVICE

(71) Applicant: Covidien LP, Mansfield, MA (US)

(72) Inventor: Masoud Molaei, Huntington, NY (US)

(73) Assignee: Covidien LP, Mansfield, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 17/810,717

(22) Filed: Jul. 5, 2022

(65) Prior Publication Data

US 2022/0330962 A1    Oct. 20, 2022

Related U.S. Application Data

(63) Continuation of application No. 16/884,665, filed on May 27, 2020, now Pat. No. 11,406,405, which is a
(Continued)

(51) Int. Cl.
*A61B 17/221* (2006.01)
*A61B 17/12* (2006.01)
(Continued)

(52) U.S. Cl.
CPC ...... *A61B 17/221* (2013.01); *A61B 17/12109* (2013.01); *A61F 2/0108* (2020.05);
(Continued)

(58) Field of Classification Search
CPC .......... A61B 17/221; A61B 2017/2212; A61B 2017/00336; A61B 2017/22034;
(Continued)

(56) References Cited

U.S. PATENT DOCUMENTS

| 740,482 A | | 10/1903 | Stare | |
|---|---|---|---|---|
| 3,108,593 A | * | 10/1963 | Glassman | ............ A61B 17/221 |
| | | | | 606/127 |

(Continued)

FOREIGN PATENT DOCUMENTS

| CA | 2607529 A1 | 4/2008 |
|---|---|---|
| CN | 101472537 A | 7/2009 |

(Continued)

OTHER PUBLICATIONS

Hill, et al., "Initial Results of the AMPLATZER Vascular Plug in the Treatment of Congenital Heart Disease, Business Briefing", US Cardiology 2004.
(Continued)

*Primary Examiner* — Kathleen S Holwerda
(74) *Attorney, Agent, or Firm* — Fortem IP LLP

(57) ABSTRACT

A device may be used for capturing and retrieving vascular debris. The device may include: at least two segments radially expandable from a collapsed state to an expanded state, each of the at least two segments having (a) a waist including a radially largest region of the segment and (b) two longitudinal ends; at least one intermediate portion, each of the at least one intermediate portion including a pivot that connects adjacent segments, each pivot having a diameter less than a diameter of the waist; wherein each of the at least two segments includes at least two struts that extend longitudinally from a proximal end to a distal end of the segment, the at least two struts tapering from the waist radially inward toward a longitudinal axis of the device as the at least two struts approach an adjacent intermediate portion.

8 Claims, 16 Drawing Sheets

Related U.S. Application Data continuation of application No. 15/934,838, filed on Mar. 23, 2018, now abandoned, which is a continuation of application No. 15/131,306, filed on Apr. 18, 2016, now Pat. No. 9,924,959, which is a continuation of application No. 13/669,652, filed on Nov. 6, 2012, now Pat. No. 9,314,248.

(51) Int. Cl.
*A61F 2/01* (2006.01)
*A61B 17/00* (2006.01)
*A61B 17/22* (2006.01)

(52) U.S. Cl.
CPC .... *A61F 2/012* (2020.05); *A61B 2017/00336* (2013.01); *A61B 2017/00778* (2013.01); *A61B 2017/22034* (2013.01); *A61B 2017/2212* (2013.01)

(58) Field of Classification Search
CPC .......... A61F 2/01; A61F 2/0108; A61F 2/012; A61F 2/013; A61F 2002/016; A61F 2002/018
See application file for complete search history.

(56) References Cited

U.S. PATENT DOCUMENTS

| | | |
|---|---|---|
| 4,425,908 A | 1/1984 | Simon |
| 4,619,246 A | 10/1986 | Molgaard-Nielsen et al. |
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsanti |
| 5,026,377 A | 6/1991 | Burton et al. |
| 5,061,275 A | 10/1991 | Wallsten et al. |
| 5,064,435 A | 11/1991 | Porter |
| 5,104,404 A | 4/1992 | Wolff |
| 5,122,136 A | 6/1992 | Guglielmi et al. |
| 5,158,548 A | 10/1992 | Lau et al. |
| 5,222,971 A | 6/1993 | Willard et al. |
| 5,250,071 A | 10/1993 | Palermo |
| 5,308,356 A | 5/1994 | Blackshear et al. |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,484,444 A | 1/1996 | Braunschweiler et al. |
| 5,499,981 A | 3/1996 | Kordis |
| 5,527,338 A | 6/1996 | Purdy |
| 5,545,208 A | 8/1996 | Wolff et al. |
| 5,545,209 A | 8/1996 | Roberts et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,662,703 A | 9/1997 | Yurek et al. |
| 5,690,671 A | 11/1997 | McGurk et al. |
| 5,702,419 A | 12/1997 | Berry et al. |
| 5,713,907 A | 2/1998 | Wholey et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,853,422 A | 12/1998 | Huebsch et al. |
| 5,855,578 A | 1/1999 | Guglielmi et al. |
| 5,879,366 A | 3/1999 | Shaw et al. |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,976,162 A | 11/1999 | Doan et al. |
| 5,980,554 A | 11/1999 | Lenker et al. |
| 6,001,092 A | 12/1999 | Mirigian et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,059,813 A | 5/2000 | Vrba et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,106,530 A | 8/2000 | Harada |
| 6,110,191 A | 8/2000 | Dehdashtian et al. |
| 6,123,715 A | 9/2000 | Amplatz |
| 6,139,564 A | 10/2000 | Teoh |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,280,412 B1 | 8/2001 | Pederson et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 | 3/2002 | Hieshima et al. |
| 6,368,339 B1 | 4/2002 | Amplatz |
| 6,375,668 B1 | 4/2002 | Gifford et al. |
| 6,379,372 B1 | 4/2002 | Dehdashtian et al. |
| 6,383,174 B1 | 5/2002 | Eder |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 | 9/2002 | Bosma et al. |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 | 3/2003 | Jacobsen et al. |
| 6,544,278 B1 | 4/2003 | Vrba et al. |
| 6,547,804 B2 | 4/2003 | Porter et al. |
| 6,551,303 B1 | 4/2003 | Van et al. |
| 6,569,179 B2 | 5/2003 | Teoh et al. |
| 6,579,302 B2 | 6/2003 | Duerig et al. |
| 6,579,303 B2 | 6/2003 | Amplatz |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,592,605 B2 | 7/2003 | Lenker et al. |
| 6,599,308 B2 | 7/2003 | Amplatz |
| 6,605,102 B1 | 8/2003 | Mazzocchi et al. |

(56) References Cited

U.S. PATENT DOCUMENTS

| | | |
|---|---|---|
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | Vantassel et al. |
| 6,652,556 B1 | 11/2003 | Vantassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | Vantassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,709,465 B2 | 3/2004 | Mitchell et al. |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |
| 6,936,055 B1 | 8/2005 | Ken et al. |
| 6,949,103 B2 | 9/2005 | Mazzocchi et al. |
| 6,949,113 B2 | 9/2005 | Van et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | Van et al. |
| 6,994,717 B2 | 2/2006 | Konya et al. |
| 7,011,671 B2 | 3/2006 | Welch |
| 7,018,401 B1 | 3/2006 | Hyodoh et al. |
| 7,029,487 B2 | 4/2006 | Greene et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | Van et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,347 B2 | 3/2010 | Kessler et al. |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | Vantassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | Van et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 8,454,681 B2 | 6/2013 | Holman et al. |
| 8,603,014 B2 | 12/2013 | Alleman et al. |
| 8,837,800 B1 | 9/2014 | Bammer et al. |
| 9,119,656 B2 | 9/2015 | Bose et al. |
| 9,126,018 B1 | 9/2015 | Garrison |
| 9,179,918 B2 | 11/2015 | Levy et al. |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,314,248 B2 | 4/2016 | Molaei |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,901,472 B2 | 2/2018 | Newell et al. |
| 9,924,959 B2 | 3/2018 | Molaei |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,478,194 B2 | 11/2019 | Rhee et al. |
| 11,406,405 B2 * | 8/2022 | Molaei ............... A61F 2/0108 |
| 2001/0000797 A1 | 5/2001 | Mazzocchi |
| 2001/0007082 A1 | 7/2001 | Dusbabek et al. |
| 2001/0012949 A1 | 8/2001 | Forber |
| 2001/0051822 A1 | 12/2001 | Stack et al. |

(56) References Cited

U.S. PATENT DOCUMENTS

| | | |
|---|---|---|
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0111647 A1 | 8/2002 | Khairkhahan et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | Vantassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1 | 10/2004 | Coyle |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0222605 A1 | 10/2005 | Greenhalgh et al. |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0217799 A1 | 9/2006 | Mailänder et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |

(56) References Cited

U.S. PATENT DOCUMENTS

| | | |
|---|---|---|
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1 | 12/2009 | Davis et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030220 A1 | 2/2010 | Truckai et al. |
| 2010/0036390 A1 | 2/2010 | Gumm |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0222802 A1 | 9/2010 | Gillespie et al. |
| 2010/0249894 A1 | 9/2010 | Oba et al. |
| 2010/0256667 A1 | 10/2010 | Ashby et al. |
| 2010/0268260 A1 | 10/2010 | Riina et al. |
| 2010/0274276 A1 | 10/2010 | Chow et al. |
| 2010/0312270 A1 | 12/2010 | Mcguckin et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0213403 A1 | 9/2011 | Aboytes |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0030461 A1 | 1/2013 | Marks et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0281788 A1 | 10/2013 | Garrison |
| 2013/0304179 A1 | 11/2013 | Bialas et al. |
| 2013/0345739 A1* | 12/2013 | Brady ............ A61B 17/320725 606/200 |
| 2014/0005713 A1 | 1/2014 | Bowman |
| 2014/0128905 A1 | 5/2014 | Molaei |
| 2014/0172001 A1 | 6/2014 | Becking et al. |
| 2014/0200648 A1 | 7/2014 | Newell et al. |
| 2014/0276074 A1 | 9/2014 | Warner |
| 2014/0277361 A1 | 9/2014 | Farhat et al. |
| 2014/0343595 A1 | 11/2014 | Monstadt et al. |
| 2015/0157331 A1 | 6/2015 | Levy et al. |
| 2015/0245932 A1 | 9/2015 | Molaei et al. |
| 2015/0359547 A1 | 12/2015 | Vale et al. |
| 2016/0015395 A1 | 1/2016 | Molaei et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0113786 A1 | 4/2016 | Levy et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |
| 2020/0281613 A1 | 9/2020 | Molaei |

FOREIGN PATENT DOCUMENTS

| | | |
|---|---|---|
| DE | 1283434 B | 11/1968 |
| DE | 102008028308 A1 | 4/2009 |
| DE | 102010050569 A1 | 5/2012 |
| DE | 102011011510 A1 | 8/2012 |
| EP | 0743047 A2 | 11/1996 |
| EP | 0855170 A2 | 7/1998 |
| EP | 0775470 B1 | 3/1999 |
| EP | 1621148 A1 | 2/2006 |
| EP | 1637176 A1 | 3/2006 |
| EP | 1752112 A1 | 2/2007 |
| EP | 1942972 A1 | 7/2008 |
| EP | 1872742 B1 | 5/2009 |
| EP | 2279023 A2 | 2/2011 |
| EP | 2363075 A1 | 9/2011 |
| EP | 2496299 A2 | 9/2012 |
| EP | 2319575 B1 | 11/2013 |
| EP | 2675402 A2 | 12/2013 |
| FR | 2890306 A1 | 3/2007 |
| JP | 2003520103 A | 7/2003 |
| JP | 2003524434 A | 8/2003 |
| JP | 2004049585 A | 2/2004 |
| JP | 2005522266 A | 7/2005 |
| JP | 2006506201 A | 2/2006 |
| JP | 2008541832 A | 11/2008 |
| JP | 4673987 B2 | 1/2011 |
| JP | 2014004219 A | 1/2014 |
| JP | 2018118132 A | 8/2018 |
| KR | 20180102877 A | 9/2018 |
| WO | 8800813 A1 | 2/1988 |
| WO | 9601591 A1 | 1/1996 |

(56) References Cited

FOREIGN PATENT DOCUMENTS

| WO | 9726939 | A1 | 7/1997 |
|---|---|---|---|
| WO | 9903404 | A1 | 1/1999 |
| WO | 9905977 | A1 | 2/1999 |
| WO | 9908607 | A1 | 2/1999 |
| WO | 9908743 | A1 | 2/1999 |
| WO | 9940873 | A1 | 8/1999 |
| WO | 9962432 | A1 | 12/1999 |
| WO | 03037191 | A1 | 5/2003 |
| WO | 02071977 | A3 | 6/2003 |
| WO | 2005117718 | A1 | 12/2005 |
| WO | 2006026744 | A1 | 3/2006 |
| WO | 2006034166 | A2 | 3/2006 |
| WO | 2006052322 | A2 | 5/2006 |
| WO | 2006091891 | A2 | 8/2006 |
| WO | 2006119422 | A2 | 11/2006 |
| WO | 2007047851 | A2 | 4/2007 |
| WO | 2007076480 | A2 | 7/2007 |
| WO | 2007095031 | A2 | 8/2007 |
| WO | 2007121405 | A2 | 10/2007 |
| WO | 2008022327 | A2 | 2/2008 |
| WO | 2008109228 | A2 | 9/2008 |
| WO | 2008151204 | A1 | 12/2008 |
| WO | 2008157507 | A2 | 12/2008 |
| WO | 2009076515 | A1 | 6/2009 |
| WO | 2009132045 | A2 | 10/2009 |
| WO | 2009134337 | A1 | 11/2009 |
| WO | 2009135166 | A2 | 11/2009 |
| WO | 2010028314 | A1 | 3/2010 |
| WO | 2010030991 | A1 | 3/2010 |
| WO | 2010147808 | A1 | 12/2010 |
| WO | 2011057002 | A2 | 5/2011 |
| WO | 2011057277 | A2 | 5/2011 |
| WO | 2011130081 | A1 | 10/2011 |
| WO | 2011153304 | A1 | 12/2011 |
| WO | 2012068175 | A2 | 5/2012 |
| WO | 2012112749 | A2 | 8/2012 |
| WO | 2012166804 | A1 | 12/2012 |
| WO | 2015141317 | A1 | 9/2015 |
| WO | 2017192999 | A1 | 11/2017 |
| WO | 2018019829 | A1 | 2/2018 |
| WO | 2018033401 | A1 | 2/2018 |
| WO | 2018046408 | A2 | 3/2018 |
| WO | 2018137029 | A1 | 8/2018 |
| WO | 2018137030 | A1 | 8/2018 |
| WO | 2018145212 | A1 | 8/2018 |
| WO | 2018156813 | A1 | 8/2018 |
| WO | 2018172891 | A1 | 9/2018 |
| WO | 2018187776 | A1 | 10/2018 |

OTHER PUBLICATIONS

Ronnen, et al., "AMPLATZER Vascular Plug Case Study, Closure of Arteriovenous Fistula Between Deep Femoral Artery and Superficial Femoral Vein", AGA Medical Corporation, May 2007.

Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

\* cited by examiner

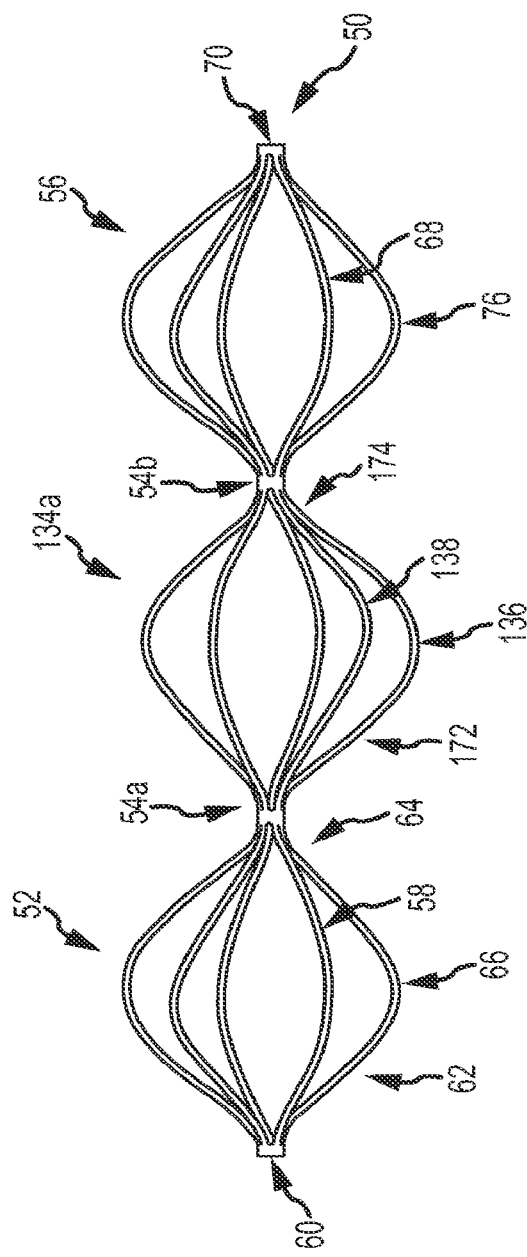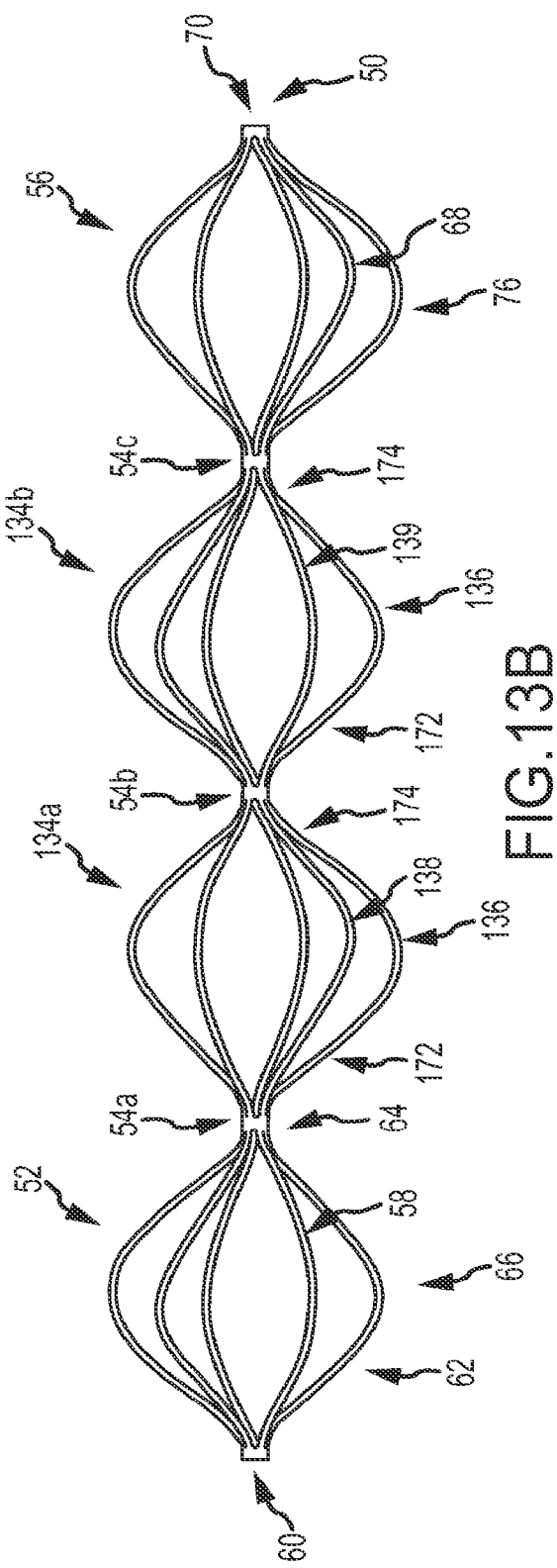

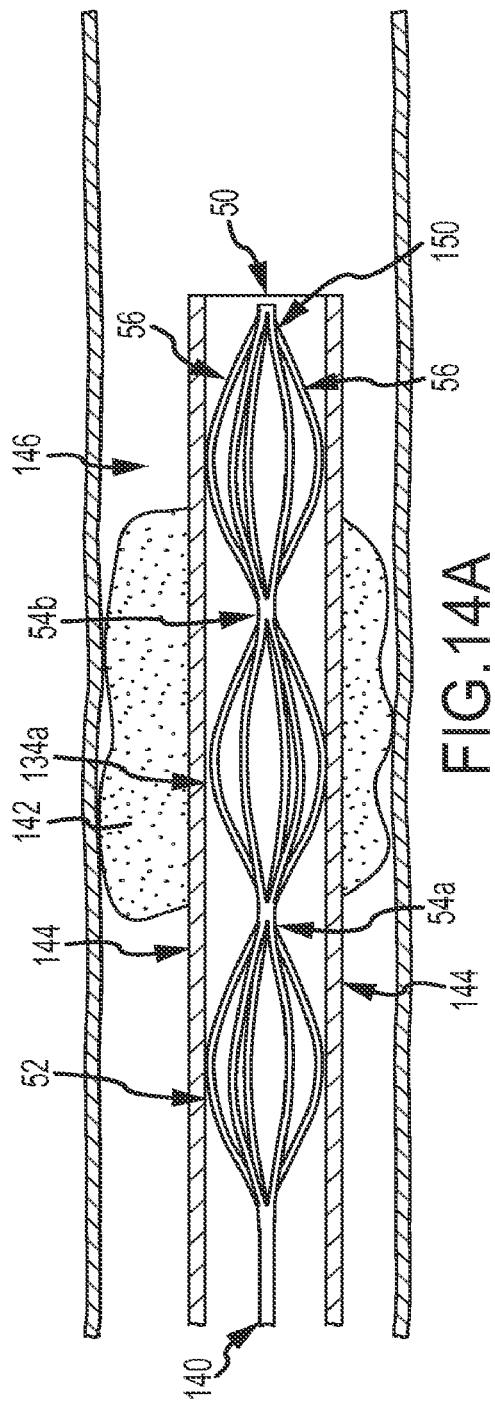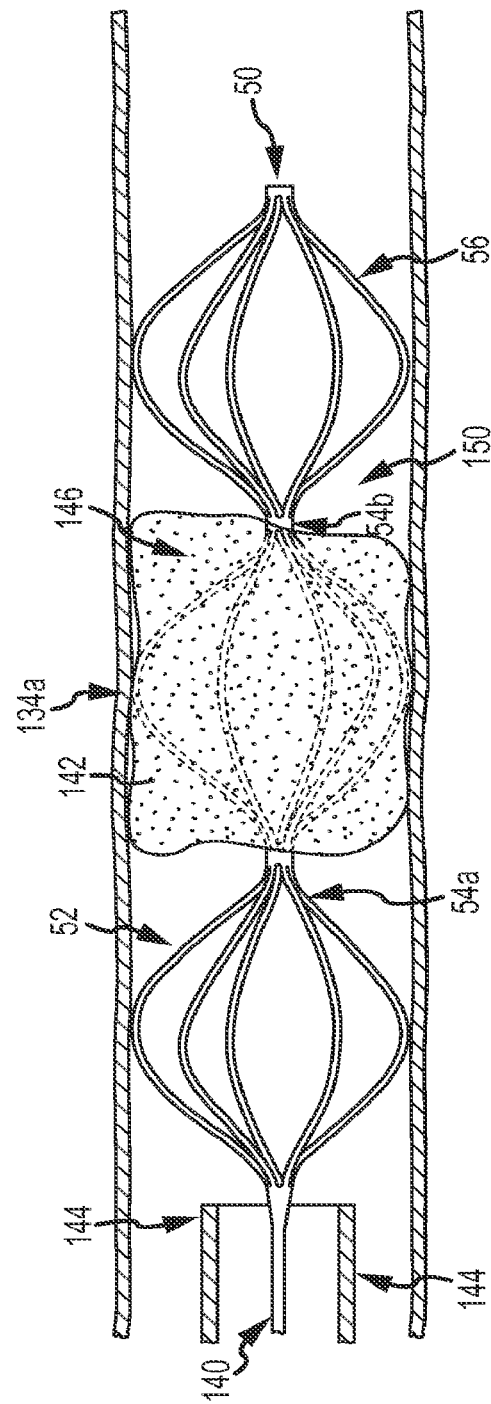

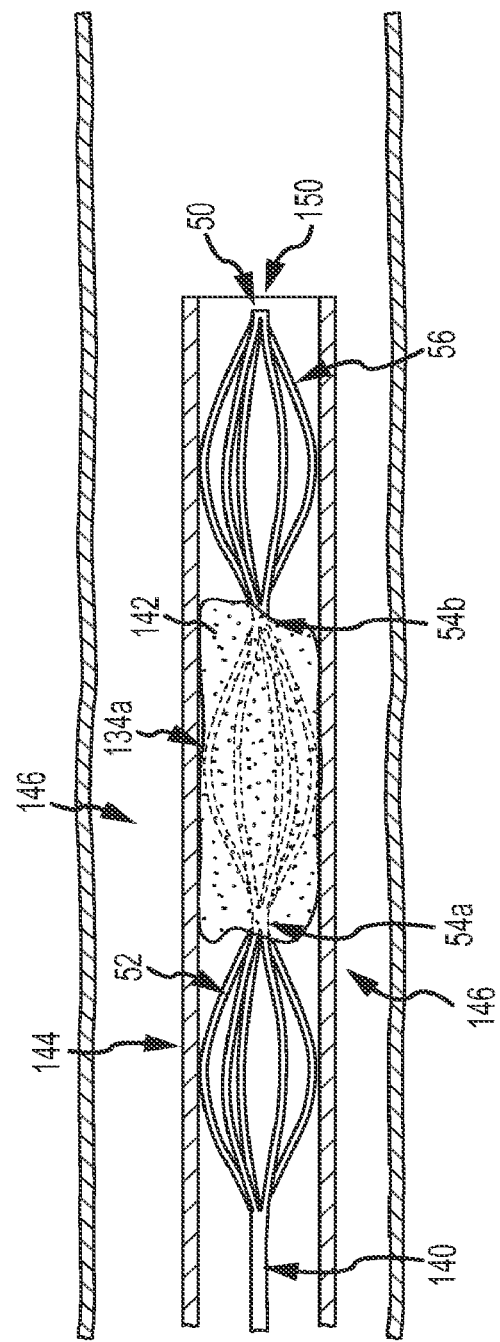

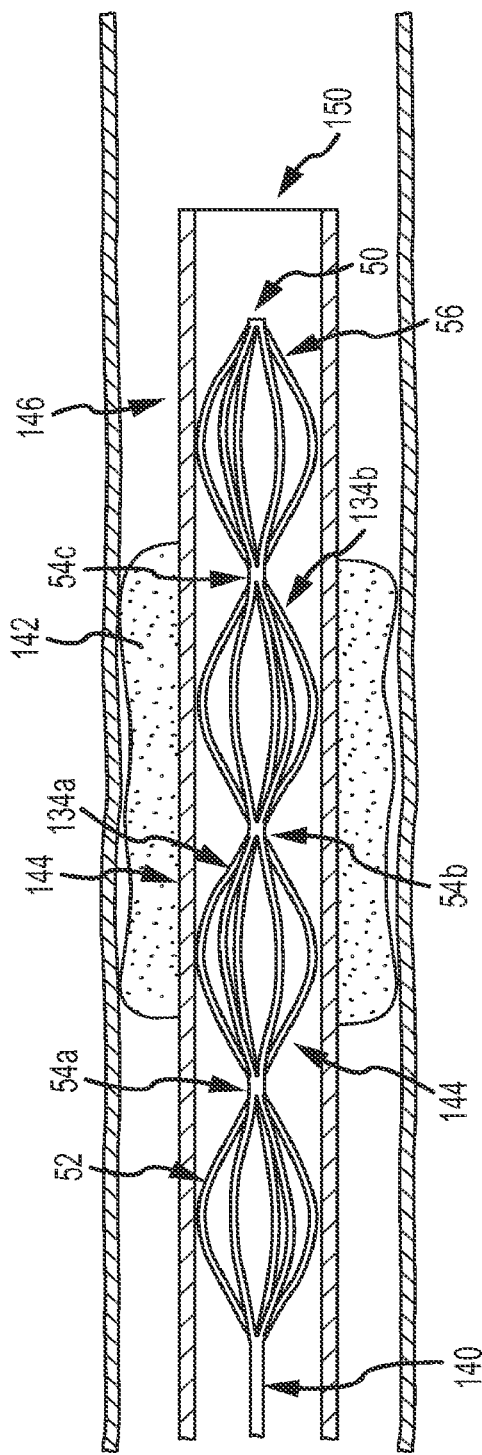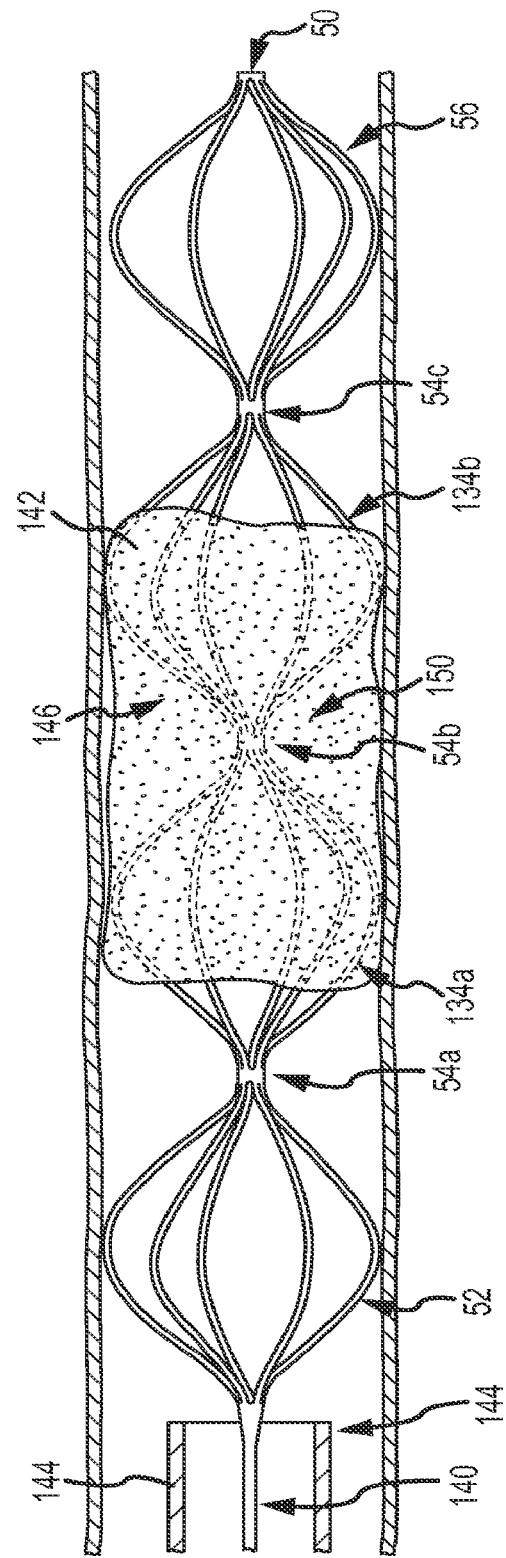

MULTI-PIVOT THROMBECTOMY DEVICE

RELATED APPLICATIONS

This application is a continuation of U.S. patent application Ser. No. 16/884,665, filed May 27, 2020, which is a continuation of U.S. patent application Ser. No. 15/934,838, filed Mar. 23, 2018, now abandoned, which is a continuation of U.S. patent application Ser. No. 15/131,306, filed Apr. 18, 2016, now issued as U.S. Pat. No. 9,924,959, which is a continuation of U.S. patent application Ser. No. 13/669,652, filed Nov. 6, 2012, now issued as U.S. Pat. No. 9,314,248, all of which are hereby incorporated by reference in their entireties.

BACKGROUND

The presence of vascular debris (e.g., thrombus, embolus) in a vasculature can cause a number of significant health problems. A thrombus is a stationary blood clot that is often found along the wall of a blood vessel and may cause vascular obstruction. Thrombus is usually formed in vivo as the final product of the blood coagulation step in hemostasis. In relatively large blood vessels, a thrombus will typically decrease the blood flow through that vessel. In smaller blood vessels, blood flow may be completely cut-off resulting in death of tissue supplied to that vessel. A dislodged thrombus is often referred to as an "embolus." Vascular obstruction or ischemia is the insufficient supply of blood to an organ, usually due to a blocked blood vessel. Symptoms of vascular obstruction may include chest pains, loss of vision, and in some cases death. Thrombectomy is a surgical procedure that involves the removal of a thrombus from a patient's vasculature.

SUMMARY

Certain vascular devices are important for their intervening roles in patients with vascular debris in their vasculature. Some techniques for removing vascular debris utilize balloon catheters, aspiration catheters, and the like. These techniques may have safety (e.g., intimal lesions) and performance issues (e.g., use limited to certain arteries). Therefore, there is a need to provide additional systems and methods for removing vascular debris from a vasculature that are safe and overcome some of the existing performance issues.

Although at least one embodiment is described herein with respect to thrombus and thrombectomy, the subject technology may be used to remove any vascular debris that is compatible with one or more embodiments with the subject technology.

The subject technology is illustrated, for example, according to various aspects described below. Various examples of aspects of the subject technology are described as embodiments. These are provided as examples and do not limit the subject technology. It is noted that these embodiments may be combined in any combination.

Some embodiments provide a system for retrieving vascular debris in a vasculature comprising at least two segments radially expandable from a collapsed state to an expanded state, each segment having a waist comprising the radially largest region of the segment and two longitudinal ends; at least one intermediate portion, each intermediate portion comprising a pivot that connects adjacent segments, each pivot having a diameter comprising the radially largest region of the pivot; an outer lumen that is configured to at least partially encapsulate the segments in the compressed state; and a tether that is configured to retrieve a segment in the expanded state into the outer lumen.

In some embodiments, at least one segment is substantially spherical. In some embodiments, the segments comprises radially-expandable struts. In some embodiments, a segment comprises at least two struts. In some embodiments, a segment comprises at least three struts. In some embodiments, a segment comprises at least four struts. In some embodiments, a segment comprises at least five struts. In some embodiments, a segment comprises at least six struts. In some embodiments, a segment comprises at least seven struts. In some embodiments, a segment comprises at least eight struts. In some embodiments, a segment comprises at least nine struts. In some embodiments, a segment comprises at least ten struts. In some embodiments, a segment comprises at least eleven struts. In some embodiments, a segment comprises at least twelve struts. In some embodiments, at least one strut diverges from the longitudinal axis, divides into at least two struts, merges with an adjacent strut, and converges toward the longitudinal axis.

Some embodiments provide a system comprising at least three segments. Some embodiments provide a system comprising at least four segments. Some embodiments provide a system comprising at least five segments. Some embodiments provide a system comprising at least six segments. Some embodiments provide a system comprising at least seven segments. Some embodiments provide a system comprising at least eight segments. Some embodiments provide a system comprising at least nine segments. Some embodiments provide a system comprising at least ten segments.

Some embodiments provide a system for retrieving vascular debris in a vasculature comprising at least three segments expandable from a collapsed state to an expanded state, each segment having a waist comprising the radially largest region of the segment and two longitudinal ends; at least two intermediate portion, each intermediate portion comprising a pivot that connects adjacent segments, each pivot having a diameter comprising the radially largest region of the pivot; an outer lumen that is configured to encase the segments in a compressed state; and a tether that is configured to retract the segments into the outer lumen.

Some embodiments provide a method of retrieving vascular debris from a vasculature comprising inserting into the vasculature of a patient at least a portion of an outer lumen comprising a distal opening and encasing at least two or more segments expandable from a collapsed state to an expanded state, each segment having a waist comprising the radially largest region of the segment and two longitudinal ends; releasing at least a portion of a segment outside the distal opening wherein at least a portion of the segment expands to engage the vascular debris; and retrieving the segment and at least a portion of the vascular debris inside the outer lumen.

In some embodiments, the vascular debris is a thrombus or an embolus. In some embodiments, the outer diameter of the outer lumen is no larger than 50% of the diameter of the vasculature.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 13A and 13B illustrate embodiments of a vascular intervention device.

FIGS. 14A, 14B, and 14C illustrate embodiments of a vascular intervention device delivery system in a vasculature.

FIGS. 15A, 15B, and 15C illustrate embodiments of a vascular intervention device delivery system in a vasculature.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

While some of the embodiments described herein specifically relate to a vascular intervention device having two segments, the described features may generally be extended to devices having two or more segments.

Vascular Intervention Device

Figure 1:
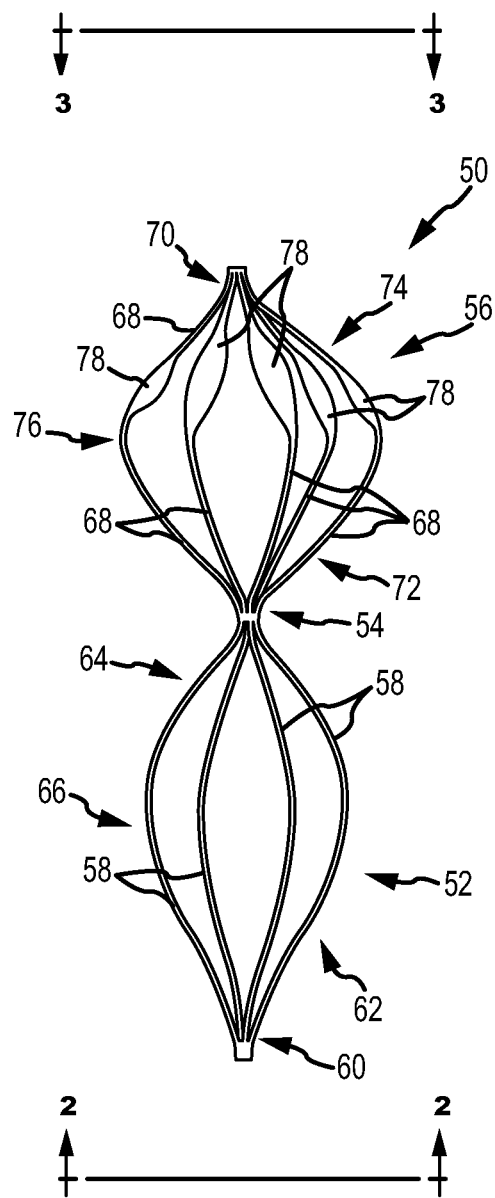
FIG. 1 illustrates embodiments of a vascular intervention device.
Figure 2:
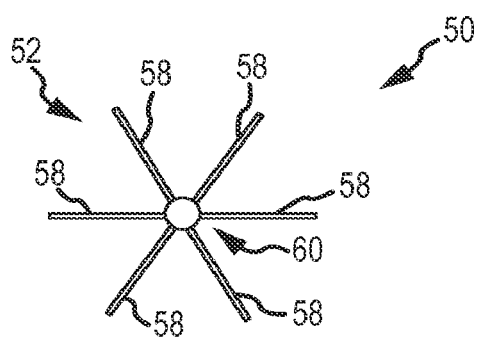
FIG. 2 illustrates a partial end view of the device of FIG. 1, taken along the direction indicated by the arrows 2-2 in FIG. 1.
Figure 3:
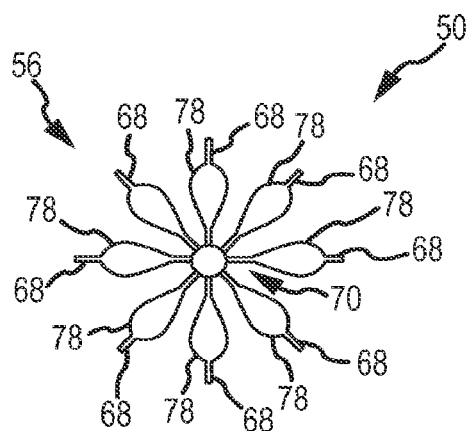
FIG. 3 illustrates a partial end view of the device of FIG. 1, taken along the direction indicated by the arrows 3-3 in FIG. 1.

FIGS. 1-3 illustrate an example embodiment of a vascular intervention device 50 that may be used to remove vascular debris (e.g., thrombus) that can obstruct the normal flow of blood in a vasculature. As illustrated in FIG. 1, the device 50 comprises two segments (a proximal segment 52 and a distal segment 56) and a pivot section 54. Referring to FIGS. 14A-15C, the device 50 can be delivered via a sheath such as a catheter 144 into the vasculature and positioned at or near a target site in order to expand, engage and retrieve vascular debris (thrombus 142). It will be appreciated that the device 50 may be more compliant than the vasculature in which it is deployed such that it may be somewhat misshapen after being deployed, and that certain shapes described herein are when the device 50 is an expanded (e.g., further expanded) state with no restriction.

While one or more embodiments described herein relate to a vascular intervention device having two segments, the device 50 may comprise any number of segments that is compatible with one or more embodiments of the subject technology. The total number of segments (one proximal, one distal, and any number of intermediate segments starting from zero) may range from about 2 to about 15 or more depending on the a number of factors such as, but not limited to, size, shape, and location of the vascular debris within a vasculature. It is generally desirable that the device 50 is at least as long as the targeted vascular debris.

FIGS. 13A-15C illustrate other embodiments of the vascular intervention device 50 that include three or more segments. As shown in FIGS. 13A and 14A-14C, the vascular intervention device 50 may have three segments, namely a proximal segment 52, a distal segment 56, and an intermediate segment 134a. FIGS. 13B and 15A-15C illustrate a vascular intervention device 50 having four segments, namely a proximal segment 52, a distal segment 56, and two intermediate segments 134a and 134b.

A vascular intervention device having a plurality of segments may provide a number of advantages related to the removal of vascular debris in a vasculature. For example, certain segments (e.g., distal, intermediate) may include widened portions 78 (FIGS. 1 and 4) that may be positioned distal to the vascular debris and filter emboli that may be generated during the use of the device 50. Moreover, a plurality of segments may also provide a greater margin for error when positioning and deploying the vascular intervention device 50 near a target site.

Proximal Segment

Referring to the embodiment illustrated in FIGS. 1 and 13A-13B, the proximal segment 52 can be radially self-expanding and may comprise a plurality of radially self-expanding struts 58. Six struts 58 are depicted in the proximal segment 52 of FIGS. 1-2 (and only four of the struts 58 are visible in FIG. 1), but more or fewer struts may be employed in the proximal segment 52, as described in further detail herein. For example, the proximal segment of FIG. 13A includes 8 struts (only five of which are visible). The struts 58 converge toward the radial center of the proximal segment 52 at the distal end of the proximal segment 52, where the proximal segment 52 joins the proximal end of the pivot section 54, and at the proximal end of the proximal segment 52, where the proximal segment 52 joins a proximal end portion 60 of the device 50.

The proximal end portion 60, located at the proximal end of the device 50, may comprise an interconnection of the proximal ends of the struts 58, which in turn can be coupled to a tether 140 (FIGS. 14A-15C) or other suitable means that facilitate deployability and/or re-sheathability and re-positionability of the device 50. Such a tether 140 may be configured to connect the device 50 to a delivery member such as a pusher wire (not shown).

When the device 50 is in a fully-expanded configuration shown in FIGS. 1-3 and 13A-13B, the proximal struts 58 extend radially outward as they advance from the proximal and distal ends of the proximal segment 52, thereby forming proximal and distal tapering portions or faces 62, 64 of the proximal segment. The struts 58 reach their radially outermost extent in a waist portion 66 of the proximal segment 52, between the proximal and distal faces 62, 64. It will be appreciated that the distal and intermediate segments may have analogous features. In the depicted waist portion 66, the struts 58 are curved and form curving radial crests or peaks. Alternatively, in the waist 66 the struts 58 can be flat and generally straight and parallel, to form an elongate and/or cylindrical waist 66.

In one or more embodiments, the struts 58 of the proximal segment 52 can have a substantially rectangular or flat cross section (e.g., where the struts 58 comprise uncut portions of a metallic tube or sheet). The struts 58 can alternatively have a substantially round (e.g., circular, elliptical, ovoid) cross section (e.g., where the struts 58 comprise round filaments). The proximal segment 52 can comprise two or more struts 58, or between two and twelve struts 58. Although the proximal segment 52 depicted in FIGS. 1-3 comprises six struts 58, the proximal segment can alternatively comprise two, three, four, five, six, seven, eight, nine, ten, eleven, or twelve struts 58. Still other numbers of struts are possible. As seen in FIG. 2, the proximal struts 58 may be equally angularly spaced and/or oriented around the central longitudinal axis of the device 50 (e.g., six struts 60.degree. apart from each adjacent strut as shown in FIG. 2, two struts 180.degree. apart from each other, three struts 120.degree. apart, four struts 90.degree. apart, etc.). Although the arrangement of the struts are shown in the figures as substantially isometric, the arrangement can place the struts in various angles relative to each other (e.g., six struts varying about 20.degree., about 40.degree., about 50.degree., about 70.degree., and about 80.degree. apart from each adjacent strut).

Figure 15C:
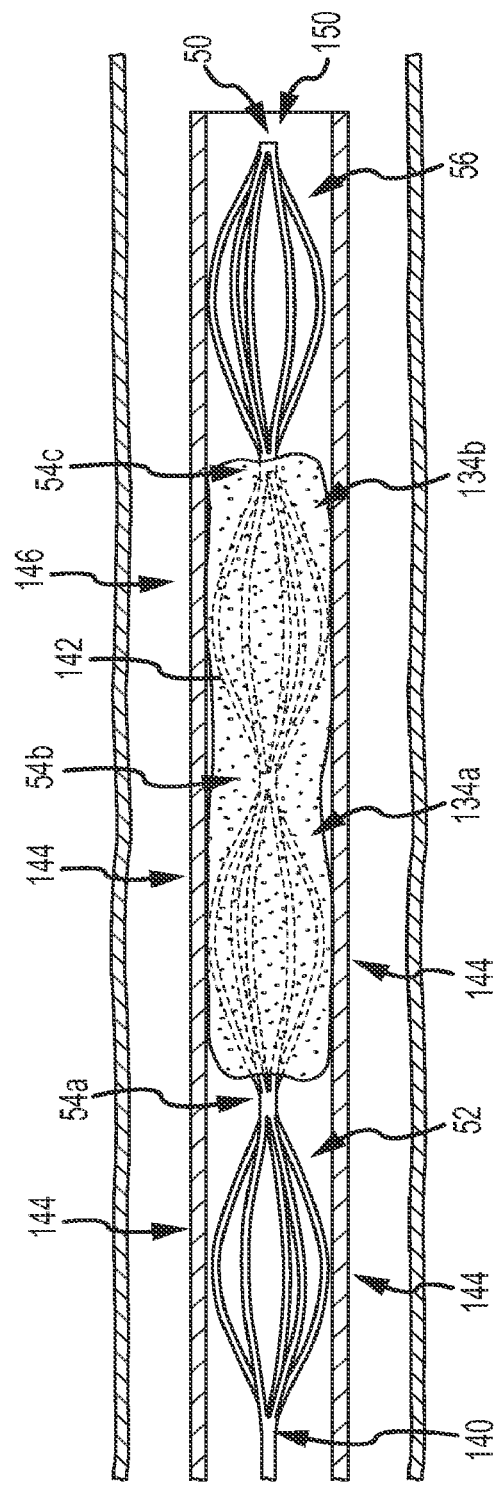

Each of the segment may be reversibly expandable from a collapsed state to an expanded state, which allows portions of the device 50 to expand after deployment and also enables the device 50 to be retrieved after deployment (FIGS. 14C and 15C). Referring to FIGS. 1 and 13A-13B, the tapered proximal face 62 of the proximal segment 52 may allow the device 50 or portions thereof (e.g., the proximal segment 52) to be retrieved back (e.g., in the proximal direction) into a delivery catheter via a distal opening thereof. For example, if the device 50 is being pulled into a catheter, the tapered proximal face 62 may radially compress the proximal segment 52. The ability to retrieve the device 50 or proximal segment 52 facilitates removal or re-positioning of the device 50 if an initial placement is not satisfactory. It will be appreciated that the distal and/or intermediate segments have similar features that also enable or facilitate the retrieval of the device into a delivery catheter via a distal opening thereof.

Distal Segment

The distal segment 56 can be radially self-expanding and comprise a plurality of radially self-expanding struts 68. Eight struts 68 are depicted in the distal section 56 of FIGS. 1, 3, and 13A-13B (and only five of the struts 68 are visible in FIG. 1), but more or fewer struts may be employed in the distal segment 56, as will be described in further detail below. The struts 68 converge toward the radial center of the distal segment 56 at the proximal end of the distal segment 56, where the distal segment 56 joins the distal end of the pivot section 54, and at the distal end of the distal segment 56, where the distal segment 56 joins a distal end portion 70 of the device 50.

When the device is in the fully-expanded configuration shown in FIGS. 1-3 and 13A-13B, each segment may include struts that extend radially outward as they advance from one end of the segment to the other end, thereby forming tapering portions or faces. For example, in FIGS. 1 and 13A-13B, the distal struts 68 extend radially outward as they advance from the proximal and distal ends of the distal segment 56, thereby forming proximal and distal tapering portions or faces 72, 74 of the distal segment 56. The struts 68 reach their radially outermost extent in a waist portion 76 of the distal segment 56, between the proximal and distal faces 72, 74.

When the device 50 is deployed in a patient's vasculature, any portion of the device such as the waist or tapering face of the distal, intermediate, and/or proximal segment may engage the vascular debris 142 (FIGS. 14A-15C). Referring to FIGS. 1 and 13A-13B, the waist portion 76, the struts 68 are curved and form curving radial crests or peaks. Alternatively, in the waist 76 the struts 68 can be flat and generally straight and parallel, to form an elongate and/or cylindrical waist 76.

The struts 68 of the distal segments can have a substantially rectangular or flat cross section (e.g., where the struts 68 comprise uncut portions of a metallic tube or sheet). FIGS. 1 and 13A-13B shows that struts 68 can alternatively have a substantially round (e.g., circular, elliptical, ovoid) cross section (e.g., where the struts 68 comprise round filaments). A circular, elliptical or ovoid cross-section may be imparted to otherwise square or rectangular struts 58/68 by processing steps such as electropolishing. The distal segment can comprise two or more struts 68, or between two and twelve struts 68. Although the distal segment 56 depicted in FIGS. 1-3 comprises eight struts 68, the distal segment can alternatively comprise two, three, four, five, six, seven, eight, nine, ten, eleven, or twelve struts 68. Still other numbers of struts are possible. As seen in FIG. 3, the distal struts 68 may be equally angularly spaced and/or oriented around the central longitudinal axis of the device 50 (e.g., eight struts 45.degree. apart from each adjacent strut, two struts 180.degree. apart from each other, three struts 120.degree. apart, four struts 90.degree. apart, etc.).

Widened Portion

One or more of the struts of a segment(s) (preferably a distal and/or an intermediate segment) can optionally include or form widened portions or leaves 78 on the distal face 74 of the distal segment. As seen in FIG. 3, the widened portions 78 can provide a blocking function to prevent or reduce the passage of materials or fluids through the distal face 74. For example, in one aspect, the widened portions 78 may be wider than a width of the struts forming the proximal face of the distal segment 56. This feature enables certain segments to act as filters to capture or engage thrombi, emboli, or other structures that form or are present after deployment of the vascular intervention device 50.

Figure 4:
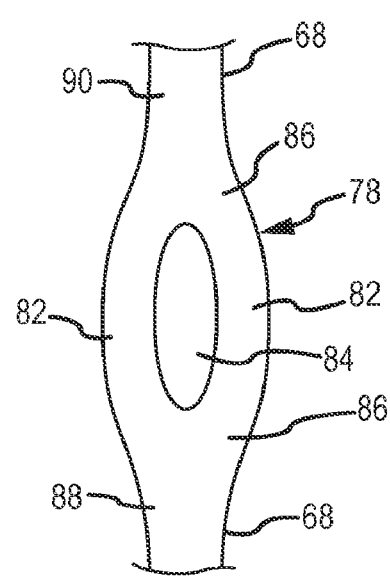
FIG. 4 illustrates an example configuration of a widened portion for use on struts of device of FIG. 1.
Figure 5:
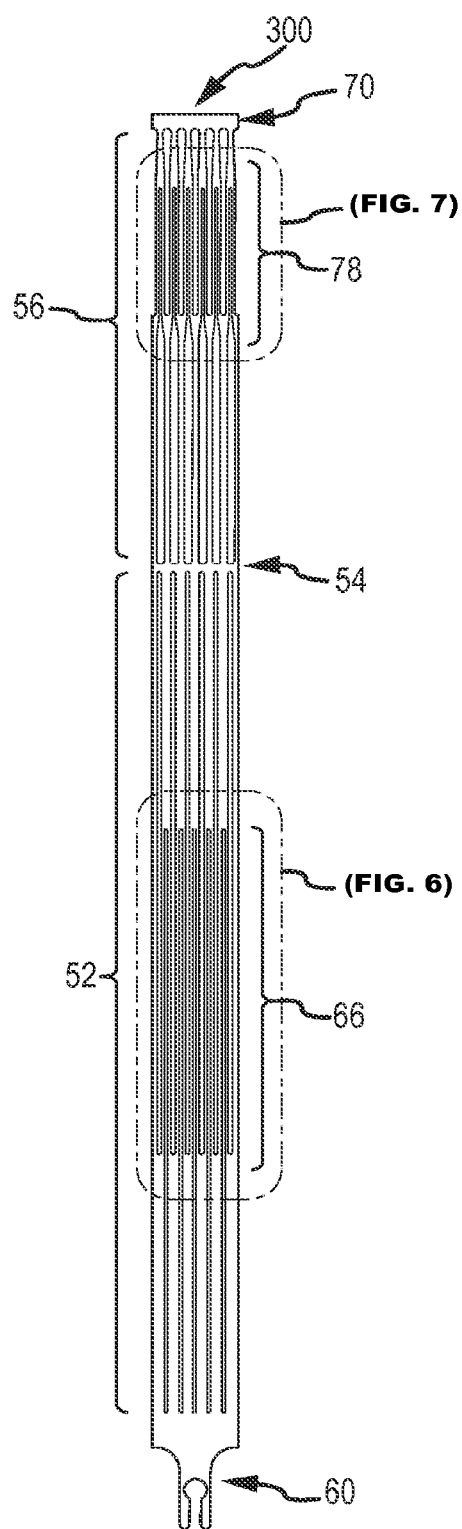
FIG. 5 illustrates a cut pattern for use in making embodiments of the device.
Figure 6:
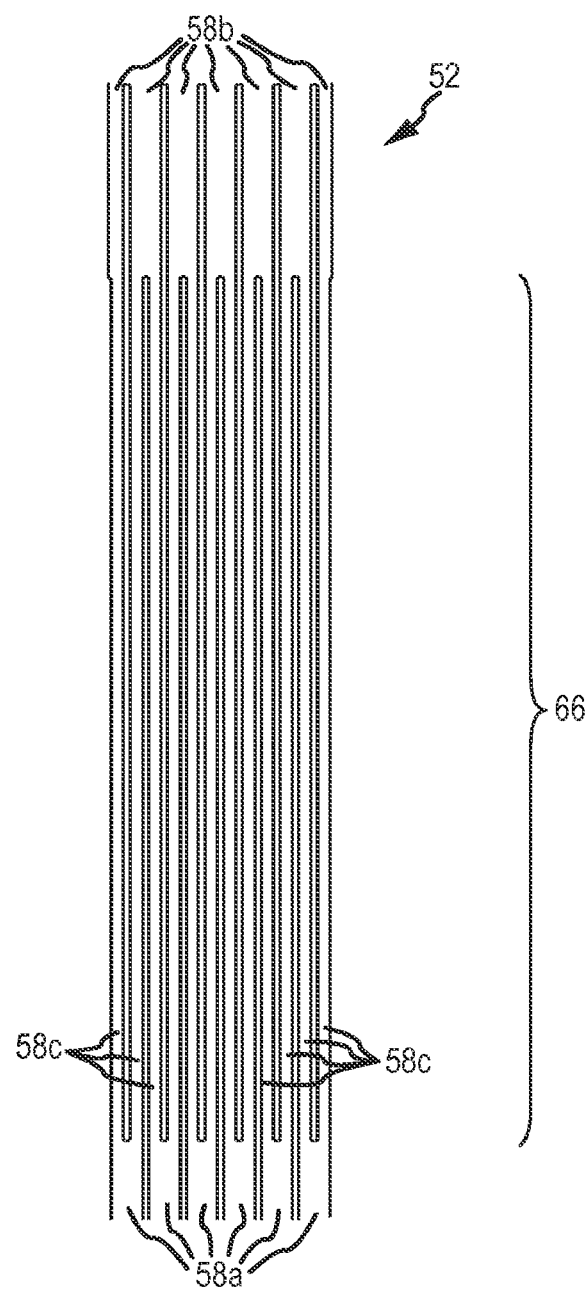
FIG. 6 illustrates a detail view of a proximal section of the cut pattern of FIG. 5.

FIG. 4 depicts one example of a widened portion 78 that may be employed with any of the embodiments of the device 50 disclosed herein. One, some or all of the widened portions 78 (and struts 68) of the device 50 may take the form depicted in FIG. 3 and further described herein. To form the widened portion 78, the strut 68 can be longitudinally split into sub-struts 82 that surround an opening 84 in the widened portion 78. The widened portions may also alternate or vary in size from one strut 68 to the next.

The struts 68 can be configured to form the sub-struts 82 and opening 84 via tapering portions 86 on either side of the opening 84. Distal and proximal of the tapering portions 86, the struts 68 can be of substantially uniform width. The proximal portion 88 of the strut 68 (proximal of the widened portion 78) can be wider than the distal portion 90 of the strut 68 (distal of the widened portion 78). In such a case, the width of the proximal strut portion 88 can nonetheless be substantially uniform from the proximal tapering portion 86 to the intermediate portion 54, and the width of the distal strut portion 90 can be substantially uniform (but narrower than the width of the proximal strut portion 88) from the distal tapering portion 86 to the distal tip portion 70 of the device 50. By employing struts 68 that are narrower in their distal portions 90 than in their proximal portions 88, the distal face of the distal portion 56 can be made relatively compliant and therefore more easily conformable, while retaining a desired degree of stiffness in the proximal components of the device 50.

In another aspect, the widened portions 78 may comprise a first and second ramp, where the first ramp extends from an edge of the strut to an edge of the widened portion 78, and the second ramp extends from the edge of the widened portion 78 to the edge of the strut. In this manner, the widened portions 78 can increase the occlusiveness of the distal face when desirable. Instead of or in addition to the widened portion(s) 78, a mesh, membrane or other covering may be employed on the distal face 74 to perform similar function(s).

Intermediate Segment

Referring to FIGS. 13A-13B, the device 50 may optionally include intermediate segment(s). The intermediate segment 134a, 134b can be radially self-expanding and comprise a plurality of radially self-expanding struts 138. Eight struts 138 are depicted in the intermediate segment 134a, 134b of FIGS. 13A-13B, but more or fewer struts may be employed in the intermediate segment 134a, 134b, as will be described in further detail below.

Referring to FIG. 13A-13B, the struts 138 converge toward the radial center of the intermediate segment 134a at the proximal end of the intermediate segment 134a, where the intermediate segment 134a joins the distal end of the pivot section 54a, and at the distal end of the intermediate segment 134a, where the intermediate segment 134a joins proximal end of pivot section 54b. Referring to FIG. 13B, the struts 139 converge toward the radial center of the intermediate segment 134b at the proximal end of the intermediate segment 134b, where the intermediate segment 134b joins the distal end of the pivot section 54b, and at the distal end of the intermediate segment 134b, where the intermediate segment 134b joins proximal end of pivot section 54c.

When the device is in the fully-expanded configuration shown in FIGS. 13A-13B, each segment may include struts that extend radially outward as they advance from one end of the segment to the other end, thereby forming tapering portions or faces. For example, in FIGS. 13A-13B, the intermediate struts 138 extend radially outward as they advance from the proximal and distal ends of the intermediate segment 134a, 134b, thereby forming proximal and distal tapering portions or faces 172, 174 of the intermediate segment 134a, 134b. The struts 138 reach their radially outermost extent in a waist portion 136 of the intermediate segment 134a, 134b, between the proximal and distal faces 172, 174.

Referring to FIGS. 13A-13B, the struts 138, 139 of the intermediate segment 134a, 134b can have a substantially rectangular or flat cross section (e.g., where the struts 138, 139 comprise uncut portions of a metallic tube or sheet). FIGS. 13A-13B show that struts 138, 139 can alternatively have a substantially round (e.g., circular, elliptical, ovoid) cross section (e.g., where the struts 68 comprise round filaments). A circular, elliptical or ovoid cross-section may be imparted to otherwise square or rectangular struts 58/68 by processing steps such as electropolishing. The intermediate segment 134a, 134b can comprise two or more struts 138, 139, or between two and twelve struts 138, 139.

In some embodiments, one or more segments (proximal, distal, and intermediate) may be substantially similar in shape. In the embodiment shown in FIGS. 13A-13B, the proximal, distal, and intermediate segments have the same number of struts. In other embodiments, the segments may comprise different number of struts. In some embodiments, a segment may have the same number of struts as at least one other segment.

Pivot Section and Pivotability

Referring to FIG. 1, the pivot section 54 connects adjacent segments (e.g., 52 and 5 in FIG. 1), and can be relatively short and relatively narrow (relative to the length and width of the proximal and distal segment 52, 56 when they are expanded). In some embodiments, the device may include one or more pivot sections that depend on the number of segments (proximal, distal, and intermediate). In the embodiment shown in FIG. 13A, the device includes two pivot sections 54a, 54b that are similar in structure to the pivot section 54 shown in FIG. 1. For example, all segments and sections and their respective parts can form a single monolithic structure. As shown in FIG. 13A, segments 52, 134a, and 56, sections 54a and 54b, and their respective parts can form a single monolithic structure. As shown in FIG. 13B, segments 52, 134a, 134b, and 56, sections 54a, 54b, and 54c, and their respective parts can form a single monolithic structure.

So configured, the pivot section (e.g., 54, 54a, 54b, 54c) allows a relatively distal segment to pivot with respect to a relatively proximal segment and thereby allow the device 50 to be deployed in tortuous vasculature. For example, referring to FIG. 1, the distal segment 56 can pivot with respect to proximal segment 52. In FIG. 13A, the distal segment 56 can pivot with respect to intermediate segment 134a and the intermediate segment 134a can pivot with respect to distal segment 56.

Referring to FIG. 1, the pivot section 54 may permit "multiaxial" pivoting or tilting, e.g. at least about a first axis through the pivot section 54 and orthogonal to the plane of the page in FIG. 1, and about a second axis through the pivot section 54 and orthogonal to the first axis. The pivot section 54 may permit "omniaxial" pivoting or tilting, about the first and second axes described above, and any radially-oriented axis passing through the pivot section 54.

The device may provide multiaxial or omniaxial pivoting or tilting up to relatively high deflection angles (e.g., up to 90 degrees) without significantly affecting the ability of the segments to maintain their expanded states and engage the vascular debris 142 (FIGS. 14A-15C). This capability can be facilitated by making the proximal struts 58 independent of the adjacent struts (e.g., distal struts 68) as depicted in FIG. 1. The two groups of struts are independent of each other in that forces acting solely on, and/or deflections occurring solely in, the proximal struts 58 do not significantly affect the ability of the distal struts 68 to maintain their expanded state, and forces acting solely on, and/or deflections occurring solely in, the distal struts 68 do not significantly affect the ability of the proximal struts 58 to maintain their expanded state.

While some of the embodiments described herein specifically relate to a vascular intervention device having two segments, the described features may generally be extended to devices having two or more segments.

Referring again to FIG. 1, one, some or all of the struts 58 can bend or pivot with respect to the pivot section 54 independently of one, some or all of the struts 68 and vice versa. The pivot section 54 may promote independence by interconnecting the struts 58 and the struts 68 in a radially central region of the device 50, and physically and functionally separating them, absorbing bending stresses from the struts 58 and the struts 68 rather than transmitting them from the struts 58 to the struts 68 or vice versa.

Instead of, or in addition to, independence of the proximal struts 58 as a group, from the distal struts 68 as a group, the struts 58 may be independent of each other (within the group of struts 58), and/or the struts 68 may be independent of each other (within the group of struts 68). In the device 50 as depicted in FIGS. 1-3, the proximal struts 58 are independent of each other and the distal struts 68 are independent of each other. Each proximal strut 58 can bend or pivot with respect to the pivot section 54 independently of the other proximal struts 58, and each distal strut 68 can bend or pivot with respect to the pivot section 54 independently of the other distal struts 68. Independence is promoted within each group of struts 58, 68 by interconnecting them only at their proximal and distal ends, and in a radially central region of the device 50.

It should be noted, however, that independence as used herein does not exclude interconnecting independent components by members (e.g. membranes, very fine wires and the like) that are insufficiently rigid to cause one component to significantly affect the action of the other. The proximal struts 58 and/or the distal struts 68 can also be independent of each other, but only within a limited region of the segment(s). For example, the proximal struts 58 may be independent of each other within the distal face 64 of the proximal segment, and/or the distal struts 68 may be independent of each other within the proximal face 72 of the distal segment 56.

The tapered distal face 64 of the proximal segment 52 and tapered proximal face 72 of the distal segment 56 also allow the sections 52, 56 to pivot significantly without contact between the segments 52, 56 other than at the pivot section 54.

The pivot section can be rigid or flexible. Where the pivot section is rigid, the pivotability of the device 50 can be provided by the flexibility and/or independence of the struts 58 in the distal face 64 of the proximal segment 52 and of the struts 68 in the proximal face 72 of the distal segment 56. In this example, the proximal and distal segments are able to pivot multiaxially relative to each other without requiring plastic deformation of the pivot section. Each of struts 58 and struts 68 may be capable of flexing, extending, bowing, straightening, bending, or other elastic or plastic deformation along the length or a portion thereof.

Referring to FIGS. 1 and 13A-13B, as struts independently flex and extend, segments 52, 56, 134a, 134b can pivot about pivot section and relative to each other. For example, struts on one side of a section may flex (e.g., bend), and struts on an opposing side of a segment may extend (e.g., straighten), whereby the segment pivots about the region where the struts connect to pivot section.

According to embodiments, such action is facilitated along one or more segments and/or sections of the device. According to embodiments, this pivot action is provided without requiring plastic deformation of pivot section or any action along the length of pivot section. The pivot section can comprise a short length of hypotube (e.g., a short length of uncut hypotube) which may be flexible or rigid. According to embodiments, the pivot section can comprise a flexible coil, longitudinally oriented such that its winds spiral around the central longitudinal axis of the device 50, or the pivot section can comprise a ball-and-socket joint, a length of flexible wire, or other flexible member.

Materials

The device 50 can further comprise one or more radiopaque markers (e.g. coils) coupled to or wound around portions of the device. For example, the device 50 can include radiopaque markers on one, two or all three of the proximal end portion 60, pivot section 54, and distal end portion 70. Instead of or in addition to those markers, the device 50 can include radiopaque markers on one or more of the struts 58, and/or on one or more of the struts 68. According to embodiments, when any of the proximal end portion 60, intermediate segment 54, or distal end portion 70 defines a central lumen therethrough (e.g., when the device 50 is cut or etched from a tube or sheet), radiopaque material may be placed within some, one or all of those lumens to make the proximal end portion 60, pivot section 54, and distal end portion 70 radiopaque. For example, radiopaque material maybe provided within a lumen of at least one of the proximal end portion 60, pivot section 54, and distal end portion 70 with securement at one or both of the ends of the lumen.

The device can comprise a self-expanding, super elastic, and/or a shape-memory material (e.g., comprising Nitinol, CoCr alloy, shape memory polymers (e.g., polyglycolic acid, polylactic acid), etc.), thereby causing the device to be self-expanding under certain conditions (e.g., when not restrained by a catheter). In some embodiments, the proximal segment, the pivot section, the distal segment, and/or intermediate segment(s) may comprise different materials. For example, the distal segment 56 may comprise polymer material while the proximal segment and the pivot section comprise metallic material, a different polymer material, etc. For another example, the distal segment may comprise metallic material while the proximal segment and the pivot section comprise different metallic materials, polymer material, etc. Other combinations of materials are also possible. The device can assume a low profile compressed state (e.g., confined within a catheter) for delivery. When cut from a tube or sheet, the device may assume substantially the diameter of the tube or rolled sheet when in the compressed state. Upon deployment from the catheter, the device expands from the compressed state to an expanded state.

The various versions of the vascular intervention device 50 disclosed herein can be manufactured in a process comprising cutting (or electrochemically etching) and shaping a metallic tube or sheet (e.g., a laser cut hypotube or sheet). A laser or electrochemical etcher may cut out portions of the tube, leaving in place the various structural elements of the proximal segment, the pivot section(s), the intermediate segment(s), and/or the distal segment. In the device 50 depicted in FIGS. 1-3 and 12, or the device 50 depicted in FIG. 4, the proximal segment 52, the pivot section 54, and the distal segment 56 can be integrally formed from a metallic tube and not cut away from each other. In devices 50 in which all segments and sections 52, 54, 56 are integrally fabricated by being cut, etched, etc. from the same tube or sheet, the device 50 is of single-piece construction, taking the form of a single, partial tube or sheet. As shown in FIGS. 1-12, all segments and sections 52, 54, 56 and their respective parts can form a single monolithic structure. For example, the proximal segment 52, the pivot section 54, and the distal segment 56 can form a single monolithic structure. Alternatively, the sections 52, 54, 56 can be formed separately and then assembled together using any suitable technique, such as welding, gluing, interlocking, crimping, swaging, braiding, deposition, etc. Where the pivot section 54 comprises a coil, the segments 52 and 56 may be formed from the same or separate tubes, and then attached to either end of the coil using any such suitable technique.

After cutting from one or more tubes, the device 50 or segments/section(s) 52/54/56 thereof may be reshaped and heat treated to impart shape setting to the device or segments/section(s). The shape setting process may include several steps comprising, for example, stretching and confining the cut tube into a new shape during the heat treatment. At the end of each heat treatment step, the cut tube assumes the shape in which it was confined during the heat treatment process. The final shape (e.g., expanded state) and size may obtained by several such steps. The device 50 or cut tube may be electropolished during manufacture, which can reduce the initial wall thickness of the tube to a final, desired thickness.

FIGS. 5-12 depict a version of the device 50 (and a cut pattern 300 for constructing it) that can be similar to any of the other versions or embodiments of the device 50 disclosed or summarized herein, in structure, configuration, function, method of manufacture, method of use, and material choice, except as further discussed herein. In the device 50 of FIGS. 5-12, the struts 58 of the proximal section 52 comprise a number (e.g. 6, as depicted, or any other suitable number) of proximal strut portions 58a and a corresponding number of distal strut portions 58b.

The proximal portions 58a and the distal portions 58b are rotated or shifted laterally with respect to each other, such that each proximal portion 58a opposes (e.g., approximately one-half of each of) two distal portions 58b, and vice versa. From the distal end of each proximal portion 58a, two sub-struts 58c extend distally to the two distal portions 58b that oppose (or are longitudinally adjacent) the proximal portion 58a from which the sub-struts 58c extend. Accordingly, each proximal portion 58a is connected to the two adjacent or opposing distal portions 58b (and vice versa) via sub-struts 58c. For example, each strut may have a proximal end, a distal end, and a center portion therebetween, the center portion connected to adjacent struts.

In another example, each strut may extend from an origination junction and be divided into a first and second branch, wherein the first branch is connected to a first adjacent strut and the second branch is connected to a second adjacent strut. In this example, a length of the first branch and a length of the second branch may be different such that a connecting point between the strut and the first adjacent strut is disposed at a different longitudinal position than a connecting point between the strut and the second adjacent strut.

According to embodiments, the length of the first branch and the length of the second branch may be the same. In another example, at least one strut may extend proximally from the intermediate section and be divided into a first and second branch at or near the waist of the proximal section. The first branch may be connected to the first adjacent strut and the second branch may be connected to the second adjacent strut. The first and second adjacent struts may extend proximally from the waist of the proximal section toward the radially central region of the device.

According to embodiments, one or more sections 52, 56 may have a first plurality of struts extending from a proximal end of the section and a second plurality of struts extending from the distal end of the section. The first and second plurality of struts may be interconnected at the waist or middle portion of the section by a third plurality of struts. Each of the first plurality of struts may be connected to two or more of the third plurality of struts. Each of the second plurality of struts may be connected to two or more of the third plurality of struts. The number of the first plurality of struts may equal the number of the second plurality of struts. The number of the third plurality of struts may be double, triple, or another multiple of one or each of the number of the first plurality of struts and the number of the second plurality of struts.

When the proximal section 52 of the device 50 is expanded, the sub-struts 58c extend both longitudinally to interconnect the proximal end portion 60 and the intermediate section 54, and laterally or circumferentially to each neighboring proximal or distal portion 58a or 58b. The resulting lateral or circumferential interconnection of the struts 58 of the proximal section 52 increases the outward radial force exerted by the proximal section 52 (and the inward radial force that the proximal section 52 can withstand without collapse) when expanded. In addition, the lateral/circumferential interconnection of the struts of the proximal section 52 reduces the tendency of the expanded struts 58 to bunch together in the vessel or "half-moon." Further, the lateral/circumferential interconnection of the struts of the proximal section maintains the three dimensional shape of the proximal section. Moreover, the lateral/circumferential interconnection of the struts of the proximal section provides structural support for the interconnected struts.

As depicted in FIGS. 5-6 and 8-9, the sub-struts 58c (e.g., the peaks thereof) can form the waist 66 of the proximal segment 52, or otherwise comprise the radially outermost portion of the proximal segment 52. The sub-struts 58c can optionally be approximately longitudinally centered on the longitudinal midpoint of the proximal segment 52, such that the midpoint approximately evenly divides the sub-struts 58c in the longitudinal direction. Such an arrangement is also depicted in FIGS. 5-6 and 8-9.

Figure 7:
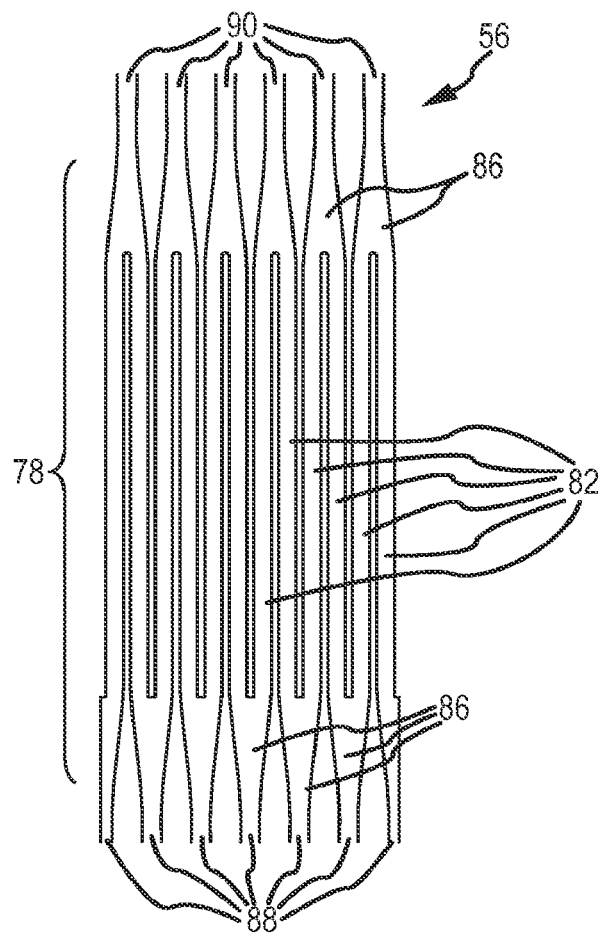
FIG. 7 illustrates a detail view of a distal section of the cut pattern of FIG. 5.
Figure 8:
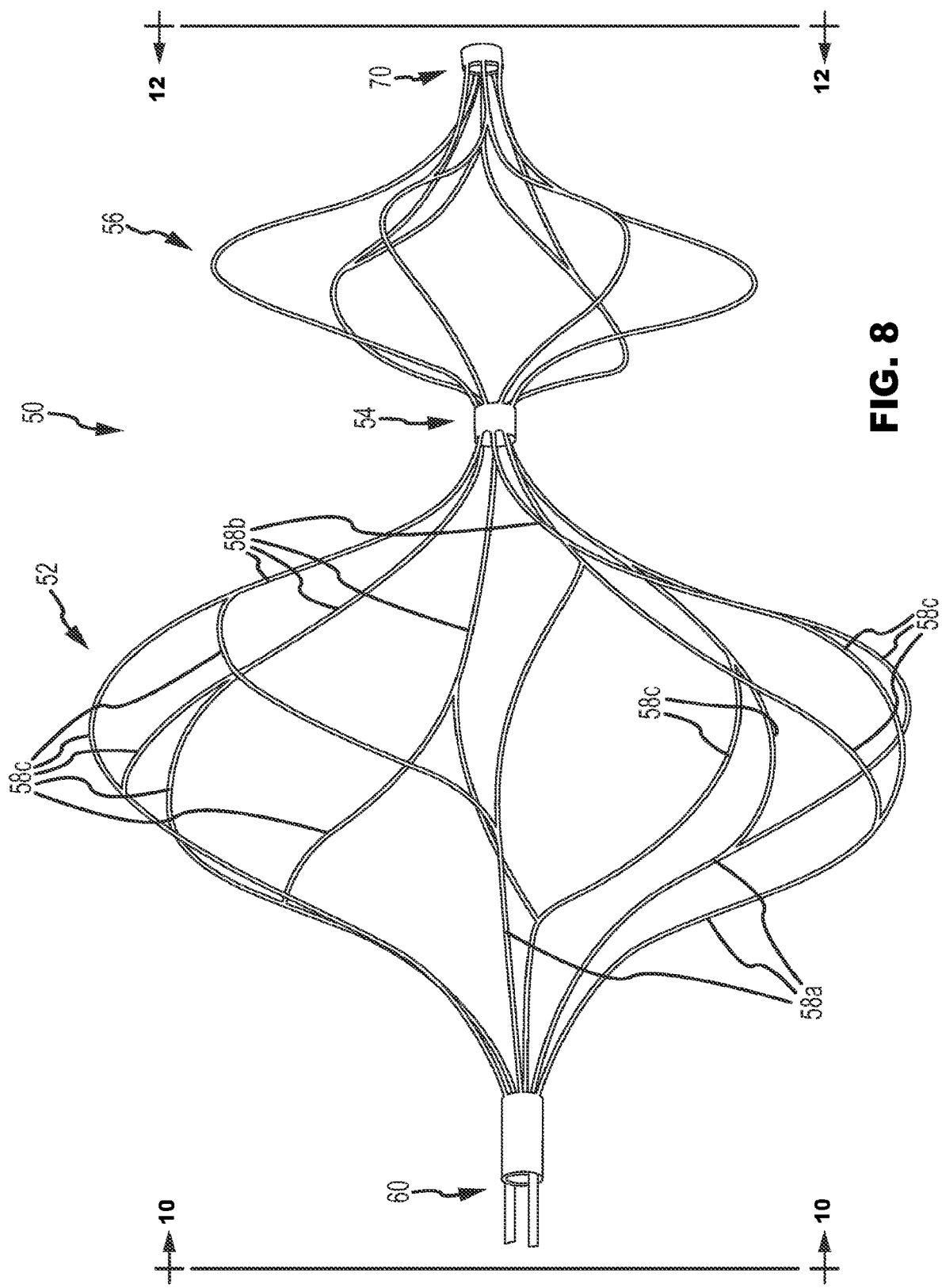
FIG. 8 illustrates a device made with the cut pattern of FIGS. 5, 6, and 7.
Figure 9:
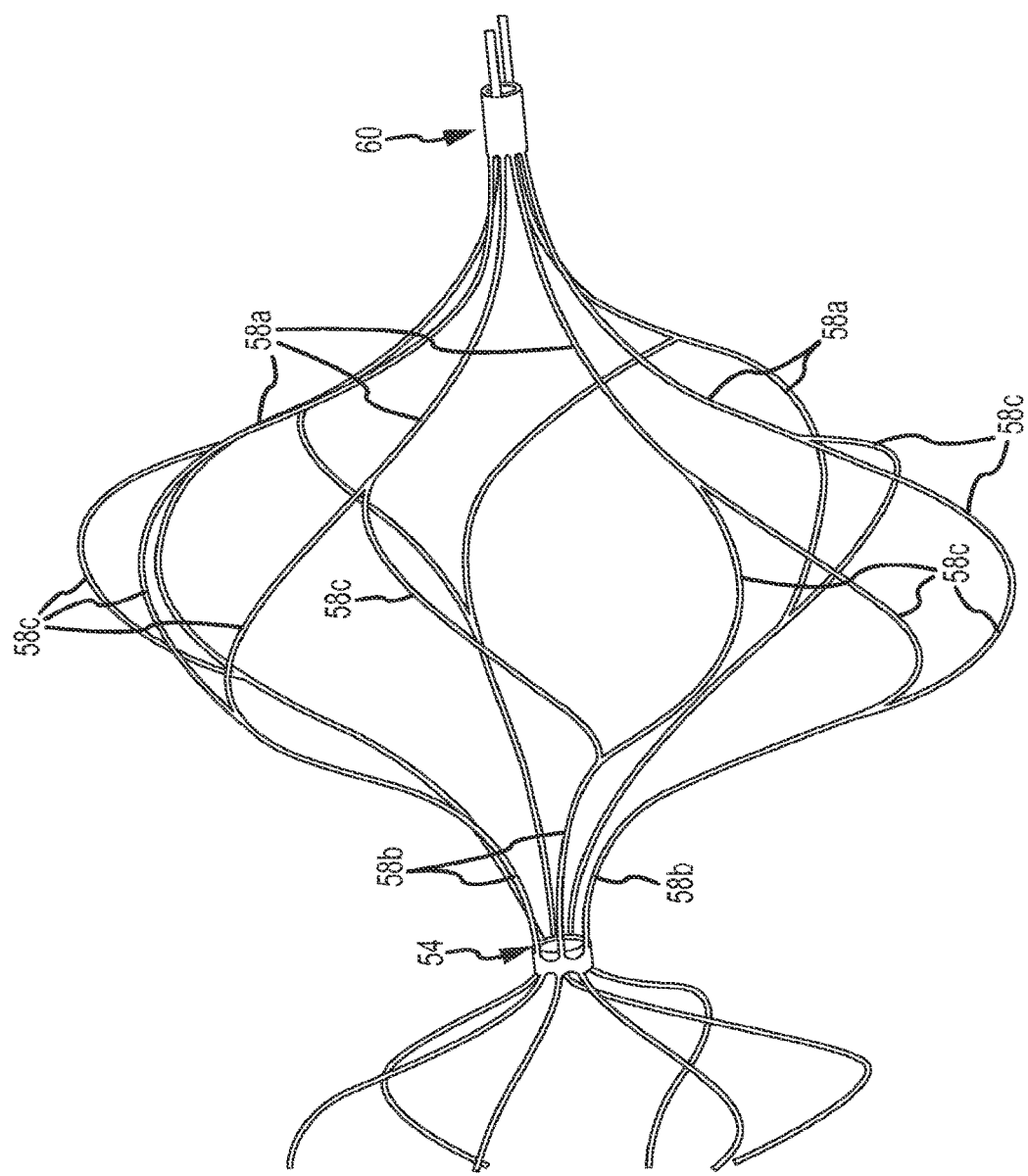
FIG. 9 illustrates a detail view of the proximal section of the device of FIG. 8.
Figure 10:
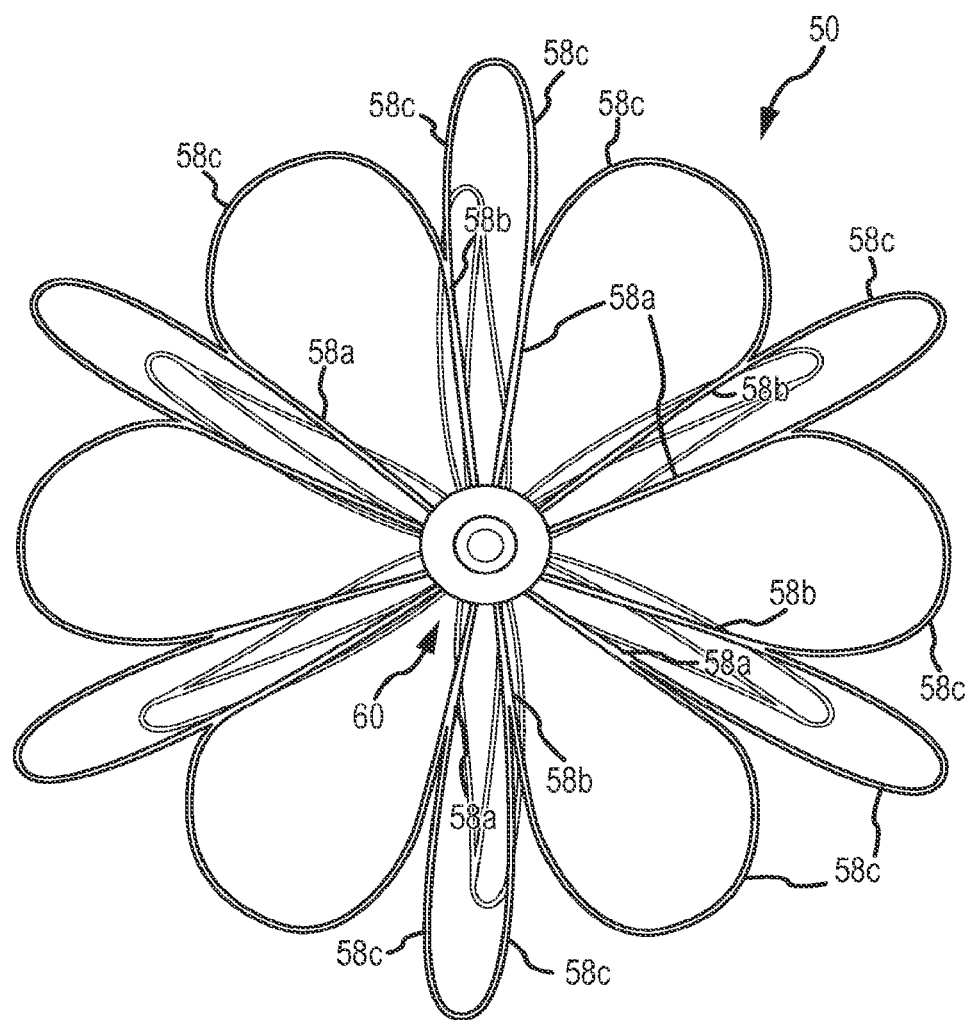
FIG. 10 illustrates a proximal end view of the proximal section of the device of FIG. 8.
Figure 11:
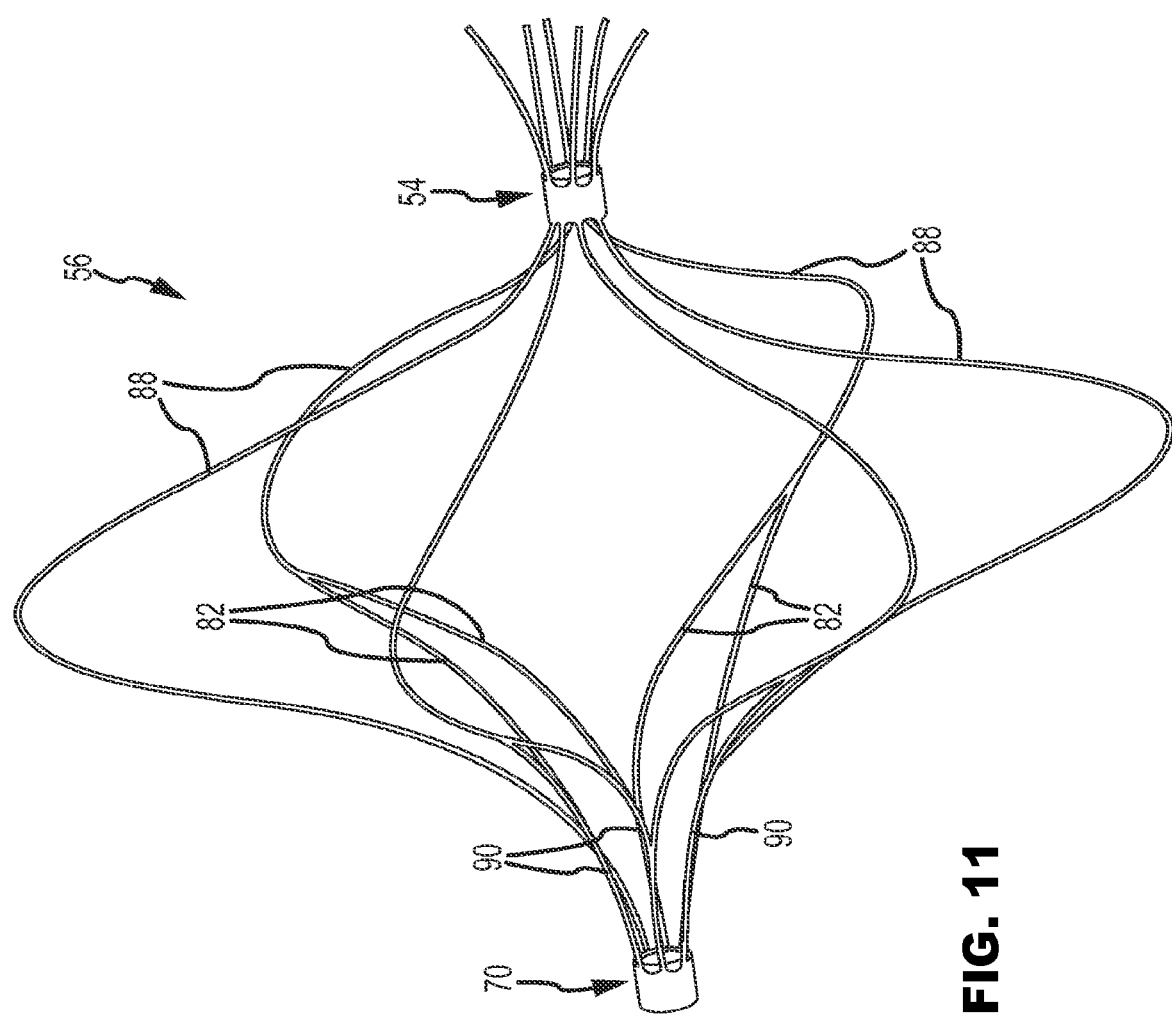
FIG. 11 illustrates a detail view of the distal section of the device of FIG. 8.
Figure 12:
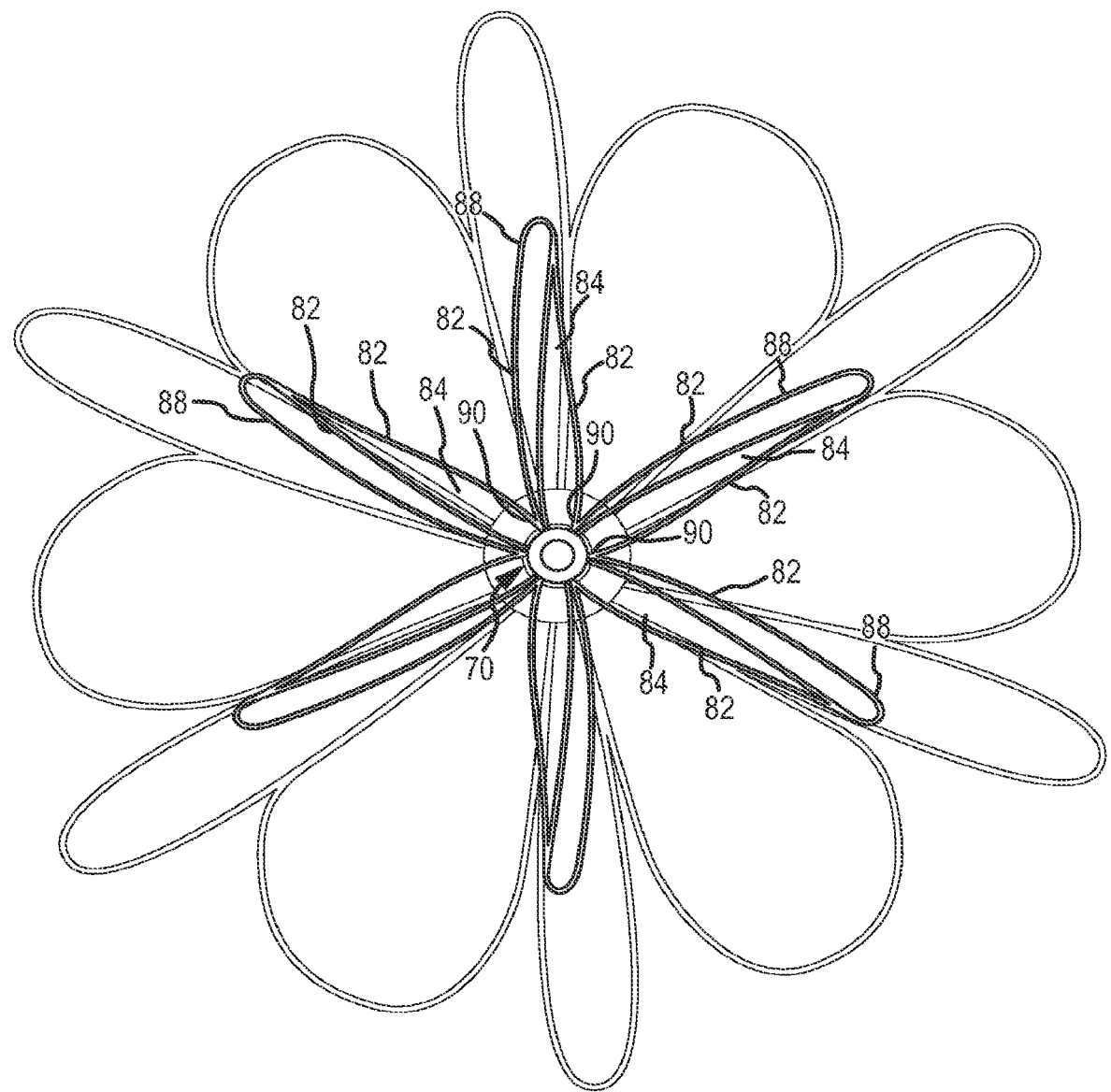
FIG. 12 illustrates a distal end view of the distal section of the device of FIG. 8.

As depicted in FIGS. 7 and 11-12, the widened portions 78 on the distal tapering portion 74 of the distal segment 56 can be formed via the lateral/circumferential interconnection arrangement employed in the proximal segment 52 and discussed above. To accomplish this, the proximal strut portions 88 and distal strut portions 90 of the distal struts 68 are rotated or shifted laterally with respect to each other, such that each proximal portion 88 opposes (e.g., approximately one-half of each of) two distal portions 90, and vice versa. From the distal end of each proximal portion 88, two sub-struts 82 extend distally to the two distal portions 88 that oppose (or are longitudinally adjacent) the proximal portion 88 from which the sub-struts 82 extend. Accordingly, each proximal portion 88 is connected to the two adjacent or opposing distal portions 90 (and vice versa) via sub-struts 82. For example, at least one strut may extend distally from the intermediate section and be divided into a first and second branch at or near the waist of the distal section. The first branch may be connected to the first adjacent strut and the second branch may be connected to the second adjacent strut. The first and second adjacent struts may extend distally from the waist of the distal section toward the radially central region of the device.

When the distal segment 56 of the device 50 of FIGS. 5-12 is expanded, the sub-struts 82 extend both longitudinally to interconnect the pivot section 54 and the distal end portion 70, and laterally or circumferentially to each neighboring proximal or distal strut portion 88 or 90. In addition, the lateral/circumferential interconnection of the struts 68 of the distal segment 56 reduces the tendency of the expanded struts 68 to bunch together once deployed in the vessel or "half-moon." Further, the lateral/circumferential interconnection of the struts of the distal segment maintains the three dimensional shape of the distal section. Moreover, the lateral/circumferential interconnection of the struts of the distal segment provides structural support for the interconnected struts.

As depicted in FIGS. 5, 7 and 11-12, the widened portions 78 and the sub-struts 82 can be located on the distal face 74 of the distal portion 56. The widened portions 78 and sub-struts 82 can optionally be located wholly distal of the waist 76 of the distal portion 56. Such an arrangement is also depicted in FIGS. 5-6 and 8-9. In other aspects, the widened portions may resemble the structures as disclosed elsewhere herein.

Dimensions

Although the device 50 is depicted in its expanded state in FIGS. 1-3, the device 50 can have a contracted state ("collapsed state") in which the proximal and distal segments 52, 56 take on a smaller diameter than in the expanded state. For example, in the contracted state the segments 52, 56 can have a diameter small enough to fit within a delivery device, such as a microcatheter. Where the segments and sections 52, 54, 56 are cut from a single tube, the diameter of one or both of the proximal and distal segments 52, 56 when in the contracted state can be substantially equal to the diameter of the tube from which the device 50 is cut, and/or substantially equal to the diameter of the pivot section 54.

The device may be of any dimension that is compatible with one or more embodiments of the subject technology. In some embodiments, the diameter of the waist (e.g., 66, 76) when expanded may be from about 2 mm to about 20 mm. In some embodiments, the diameter of the waist when contracted may be from about 0.25 mm to about 0.75 mm. In some embodiments, the length of the a segment when expanded may be from about 2 mm to about 20 mm. In some embodiments, the width of a strut may be from about 0.075 mm to about 0.15 mm. In some embodiments, the thickness of a strut may be from about 0.025 mm to about 0.10 mm. In some embodiments, the length of the pivot section may be from about 0.01 mm to about 5 mm. In some embodiments, the diameter of the pivot section may be from about 0.25 mm to about 0.75 mm. In some embodiments, the wall thickness of the pivot section may be from about 0.025 mm to about 0.10 mm.

Thrombectomy Embodiments

In the embodiment shown in FIGS. 14A-14C, the vascular intervention device 50 is at least partially encapsulated by a sheath (e.g., catheter 144) which has been inserted into a vasculature 146. As shown in FIG. 14A, the vascular intervention device 50 is in a collapsed state and the catheter 144 is positioned at or near vascular debris 142 which resides within a vasculature 146. FIG. 14A represents one possible configuration of vascular intervention device 50 prior to its deployment from the catheter 144. As shown in FIGS. 14A-14B and 15A-15B, the thrombus 142 is adhered to an inner wall of the vasculature 146.

FIG. 14B shows a vascular intervention device 50 in a deployed or partially-deployed state. As shown in FIG. 14B, the distal segment 56 has been moved distally outside of the distal opening 150 of the catheter 144 and is now in an expanded state. A distal or proximal motion of the vascular intervention device 50 is generally initiated by a user who can controllably operate the device 50 at the proximal end (not shown) and may be accomplished by any number of means, for example, proximal motion of the catheter 144, distal motion of the device 50, or both. A user may operate an actuator which is coupled to a tether 140 which in turn is coupled to the device 50 as shown in FIGS. 14A-14C. As shown in FIG. 14B, the distal segment 56 can expand to the expanded state and engage a thrombus 142. In the particular embodiment shown in FIG. 14B, a portion of the vascular intervention device 50 is still encapsulated by the sheath. In other embodiments, the vascular intervention device may be fully deployed, in which all of the segments have been pushed outside the distal opening 150 of the catheter 144. FIG. 14C shows the vascular intervention device in a re-collapsed state. As shown in FIG. 14C, the vascular intervention device 50 has moved proximally (relative to FIG. 14B) back into the catheter 144 through the distal opening 150 after engaging the thrombus 142 in FIG. 14B. The proximal motion of the device 50 effectively retrieved the thrombus 142 into the catheter 144. The proximal movement caused the expanded segment(s) to revert back to a collapsed state. Suction, aspiration, or negative pressure may be provided as thrombus 142 is brought near distal opening 150, to facilitate capture of thrombus 142 within catheter 144. Further, balloon devices, such as balloon catheters, may be provided and utilized to manage flow through the vasculature at the location of thrombus 142. For example, a balloon may be expanded proximal to distal opening 150 to substantially slow or stop flow downstream to the location of thrombus 142. Use of a balloon and aspiration creates a flow path that facilitates capture of thrombus 142 within catheter 144.

In the embodiment shown in FIGS. 15A-15C, the vascular intervention device 50 includes four segments that are at least partially encapsulated by the catheter 144 which has been inserted into a vasculature 146. The segments are coupled to a tether 140 which can be manipulated by a user to causes proximal or distal translational motions of the device 50. As shown in FIG. 15A, the vascular intervention device 50 is in a collapsed state and the catheter 144 is positioned at or near a thrombus 142 which resides within a vasculature 146.

FIG. 15B shows a vascular intervention device 50 in a deployed or partially-deployed state. As shown in FIG. 15B, the distal and the intermediate segments have been moved distally outside of the distal opening 150 of the catheter 144 and are now in an expanded state. In the embodiment shown in FIG. 15B, the distal segment 56 has been deployed distal to the thrombus 142 while the intermediate segment is positioned to engage the thrombus 142. One of the advantages of multiple segments is that relatively less precision is required during the positioning process since any of the segments can engage the thrombus. Optionally, the relatively distal segments may act as a filter by having, for example, widened portions that increase the occlusiveness of the distal segment. Thus, parts of thrombus that may be broken up during the engagement of the intermediate segment to the thrombus may be filtered downstream by the distal segment. In the embodiment shown in FIG. 15B, a proximal portion of the vascular intervention device 50 is still encapsulated by the catheter 144. In other embodiments, the vascular intervention device 50 may be fully deployed. FIG. 15C shows the vascular intervention device 50 in a re-collapsed state. As shown in FIG. 15C, the vascular intervention device 50 has moved proximally through the distal opening 150 after engaging the thrombus in FIG. 15B. The proximal movement caused the expanded segment(s) to revert back to a collapsed state and effectively retrieved the thrombus 142 into the catheter 144.

Some embodiments provide a device for retrieving vascular debris in a vasculature comprising: at least two segments radially expandable from a collapsed state to an expanded state, each segment having a waist comprising the radially largest region of the segment and two longitudinal ends; at least one intermediate portion, each intermediate portion comprising a pivot that connects adjacent segments, each pivot having a diameter comprising the radially largest region of the pivot; a sheath that is configured to encase the segments in the compressed state; and a tether that is configured to retract the expanded segment into the outer sheath.

In some embodiments, the struts are radially-expandable. In some embodiments, at least one strut diverges from the longitudinal axis, divides into at least two struts, merges with a circumferentially adjacent strut, and converges toward the longitudinal axis.

Some embodiments provide a device comprising at least three segments. Some embodiments provide a device comprising at least four segments. Some embodiments provide a device comprising at least five segments. Some embodiments provide a device comprising at least six segments. Some embodiments provide a device comprising at least seven segments. Some embodiments provide a device comprising at least eight segments. Some embodiments provide a device comprising at least nine segments. Some embodiments provide a device comprising at least ten segments.

Some embodiments provide a device for retrieving vascular debris in a vasculature comprising: at least three segments expandable from a collapsed state to an expanded state, each segment having a waist comprising the radially largest region of the segment and two longitudinal ends; at least two intermediate portion, each intermediate portion comprising a pivot that connects adjacent segments, each pivot having a diameter comprising the radially largest region of the pivot; a sheath that is configured to encase the segments in a compressed state; and a tether that is configured to retract the segments into the sheath.

Some embodiments provide a method of retrieving vascular debris from a vasculature comprising: inserting into the vasculature of a patient at least a portion of a sheath comprising a distal opening and encasing at least two or more segments expandable from a collapsed state to an expanded state, each segment having a waist comprising the radially largest region of the segment and two longitudinal ends; releasing at least a portion of a segment outside the distal opening wherein at least a portion of the segment expands to engage the vascular debris; and retrieving the segment and at least a portion of the vascular debris inside the sheath.

In some embodiments, the vascular debris is a thrombus or an embolus. In some embodiments, the sheath encapsulates at least three expandable segments. In some embodiments, the outer diameter of the sheath is no larger than 50% of the diameter of the vasculature.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

Furthermore, to the extent that the term "include," "have," or the like is used in the description or the claims, such term is intended to be inclusive in a manner similar to the term "comprise" as "comprise" is interpreted when employed as a transitional word in a claim.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

I claim:

1. A device for retrieving vascular debris in a vasculature, the device comprising:
   a monolithic structure comprising a plurality of first struts and a plurality of openings between the first struts, the monolithic structure comprising a plurality of portions, the portions including a proximal portion, an intermediate portion, and a distal portion, wherein each of the portions has a waist region corresponding to a radially largest region of the respective portion;

an intermediate member extending between adjacent ones of the portions of the monolithic structure, wherein the intermediate member comprises a hollow tubular structure and has a diameter less than a diameter of each of the waist regions; and a plurality of second struts continuous with a distal end portion of the intermediate member, the plurality of second struts being longitudinally aligned with the distal portion of the monolithic structure, wherein the device is radially expandable from a collapsed state to an expanded state, and wherein, at least when the device is in the expanded state, the proximal portion of the monolithic structure comprises a proximal end portion having a cross-sectional dimension that decreases in a proximal direction, an open distal end portion, and a generally tubular intermediate portion between the proximal and distal end portions of the proximal portion of the monolithic structure, the intermediate portion of the monolithic structure comprises a proximal end portion having a cross-sectional dimension that decreases in a proximal direction, an open distal end portion, and a generally tubular intermediate portion between the proximal and distal end portions of the intermediate portion of the monolithic structure, the distal portion of the monolithic structure comprises a proximal end portion having a cross-sectional dimension that decreases in a proximal direction, a distal end portion having a cross-sectional dimension that decreases in a distal direction, and a generally tubular intermediate portion between the proximal and distal end portions of the distal portion of the monolithic structure, wherein the intermediate portion of the distal portion of the monolithic structure comprises the waist region of the distal portion of the monolithic structure, and each second strut of the plurality of second struts comprises a proximal region extending radially outwardly from a proximal end to a distal end at a crest region of the second strut and a distal region extending radially inwardly from a proximal end at the crest region to a distal end, the crest region being located at a radial distance from a longitudinal axis of the device greater than a radius of the intermediate member and less than a radius of the waist region of the distal portion of the monolithic structure, wherein the proximal region and the distal region of the second strut are convex towards the longitudinal axis and the crest region of the second strut is concave towards the longitudinal axis.

2. The device of claim 1, wherein the distal end portion of the distal portion of the monolithic structure comprises a closed end.

3. The device of claim 1, wherein, when the device is in the expanded state, the proximal and intermediate portions of the monolithic structure have substantially similar cross-sectional dimensions at their respective waist regions.

4. The device of claim 1, wherein the proximal and intermediate portions of the monolithic structure have the same number of first struts.

5. The device of claim 1, wherein each of the portions of the monolithic structure is axisymmetric about a longitudinal axis of the device.

6. The device of claim 1, wherein the distal portion of the monolithic structure is more occlusive than each of the proximal and intermediate portions of the monolithic structure.

7. The device of claim 1, wherein adjacent second struts of the plurality of second struts are spaced apart around a circumference of the device by about 90 degrees.

8. The device of claim 1, wherein the diameter of the intermediate member is substantially constant along a length of the intermediate member.

* * * * *